(12) United States Patent
Moriya et al.

(10) Patent No.: US 8,157,778 B2
(45) Date of Patent: Apr. 17, 2012

(54) ABSORBENT ARTICLE

(75) Inventors: Reiko Moriya, Kanagawa (JP); Migaku Suzuki, Kanagawa (JP)

(73) Assignee: Daio Paper Corporation, Shikokuchuo-shi (JP)

( * ) Notice: Subject to any disclaimer, the term of this patent is extended or adjusted under 35 U.S.C. 154(b) by 39 days.

(21) Appl. No.: 10/570,028

(22) PCT Filed: Aug. 18, 2005

(86) PCT No.: PCT/JP2005/015070
§ 371 (c)(1),
(2), (4) Date: Mar. 1, 2006

(87) PCT Pub. No.: WO2006/019138
PCT Pub. Date: Feb. 23, 2006

(65) Prior Publication Data
US 2006/0241557 A1    Oct. 26, 2006

(30) Foreign Application Priority Data
Aug. 19, 2004    (JP) ................................ 2004-239172

(51) Int. Cl.
*A61F 13/15*    (2006.01)
*A61F 13/20*    (2006.01)

(52) U.S. Cl. ........ 604/385.101; 604/385.01; 604/385.16

(58) Field of Classification Search ............. 604/385.01, 604/385.101, 378
See application file for complete search history.

(56) References Cited

U.S. PATENT DOCUMENTS

| 4,781,711 | A | 11/1988 | Houghton et al. |
| 6,383,170 | B1 | 5/2002 | Mishima et al. |
| 6,458,114 | B1 | 10/2002 | Mishima et al. |
| 6,498,283 | B1 | 12/2002 | Wada et al. |
| 6,835,192 | B1 * | 12/2004 | Guidotti et al. ......... 604/385.101 |
| 6,926,703 | B2 * | 8/2005 | Sugito et al. ........... 604/385.101 |
| 7,175,613 | B2 * | 2/2007 | Sugiyama et al. ....... 604/385.14 |

FOREIGN PATENT DOCUMENTS

| JP | A 62-167562 | 7/1987 |
| JP | U 5-33717 | 5/1993 |
| JP | U 5-48922 | 6/1993 |
| JP | A 06-090977 | 4/1994 |
| JP | A 09-028732 | 2/1997 |
| JP | A 9-84816 | 3/1997 |
| JP | B2 2757931 | 3/1998 |
| JP | A 10-295723 | 11/1998 |
| JP | A 2000-116703 | 4/2000 |
| JP | A 2000-325394 | 11/2000 |
| JP | B2 3144514 | 1/2001 |
| JP | A 2001-70342 | 3/2001 |
| JP | A 2001-137286 | 5/2001 |
| JP | B2 3433770 | 5/2003 |
| JP | B2 3507848 | 1/2004 |
| WO | WO 02-24130 A1 | 3/2002 |

* cited by examiner

Primary Examiner — Michele M Kidwell
(74) Attorney, Agent, or Firm — Oliff & Berridge, PLC

(57) ABSTRACT

Disclosed is an absorbent article including: a first sheet leak preventer; a second sheet leak preventer present above and in a rear part of the first leak preventer; and an absorbent containing a super absorbent polymer, capable of absorbing a body fluid, and provided above the first leak preventer extending from a front part of the first leak preventer beneath the second leak preventer in at least one layer. The absorbent article of the present invention can separate urine and feces efficiently in use and having high urine absorption capacity.

16 Claims, 34 Drawing Sheets

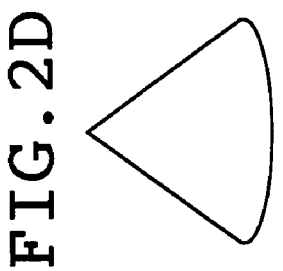
FIG. 2D
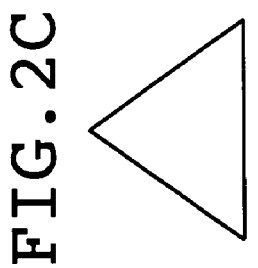
FIG. 2C
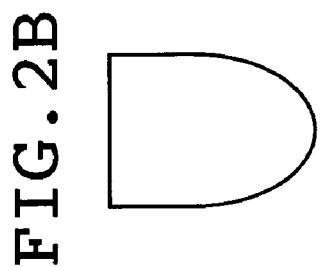
FIG. 2B
FIG. 2A
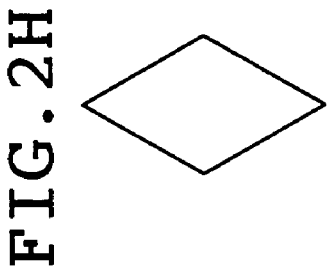
FIG. 2H
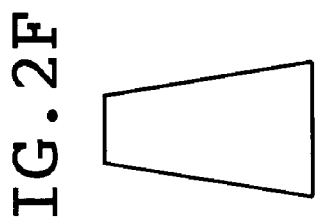
FIG. 2G
FIG. 2F
FIG. 2E
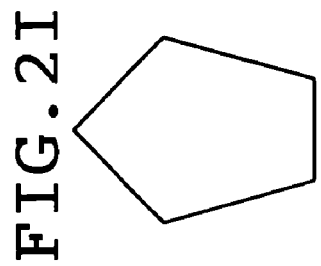
FIG. 2J
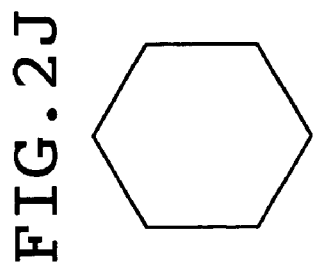
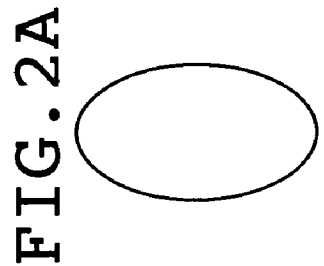
FIG. 2I
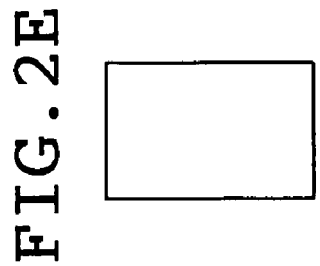

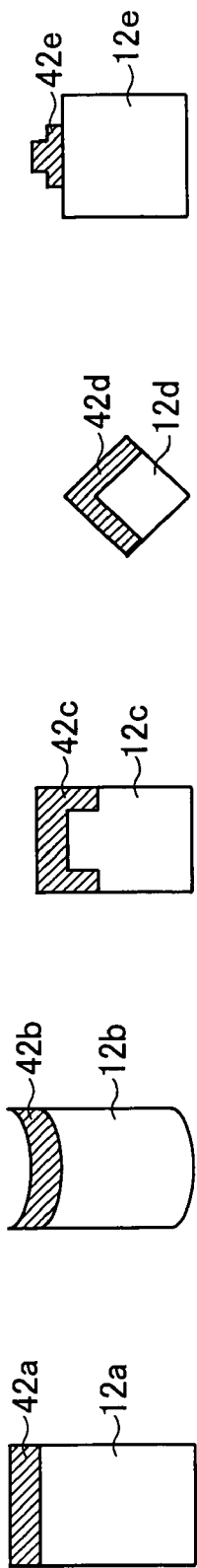
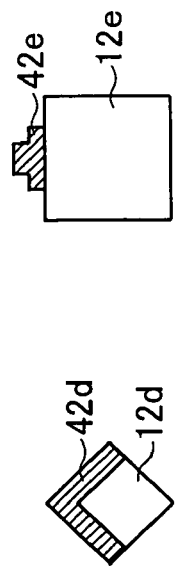
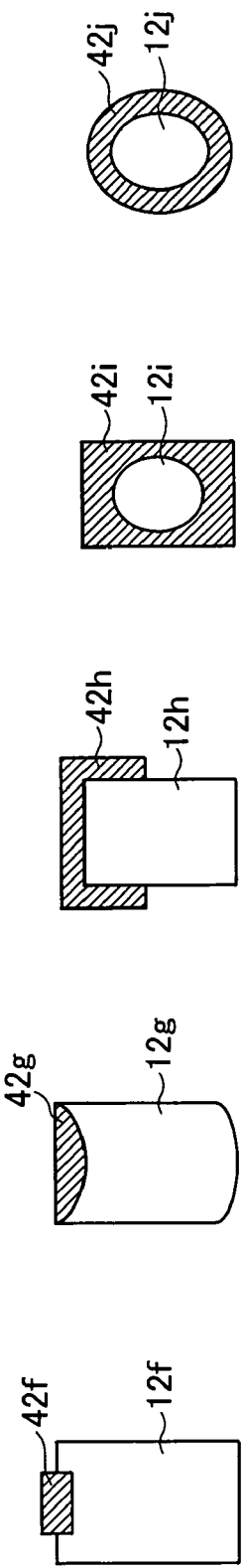
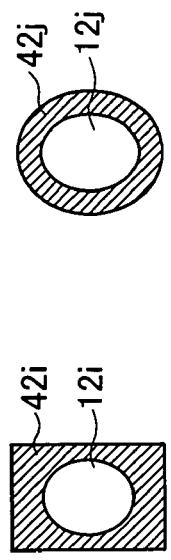
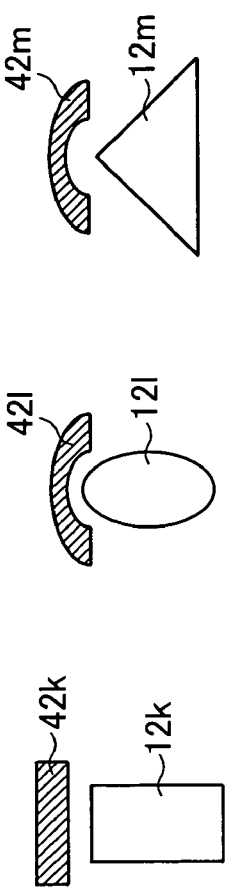

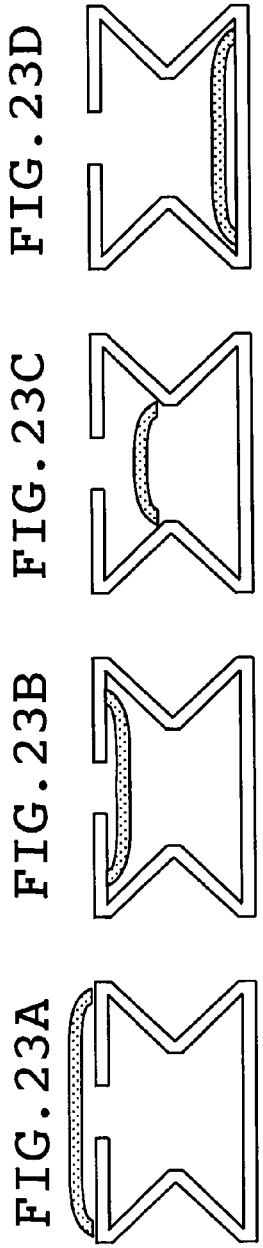

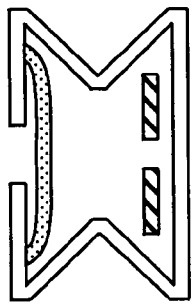
FIG. 24B
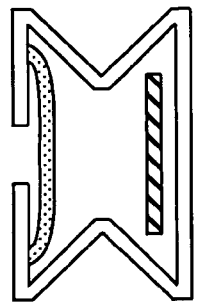
FIG. 24A
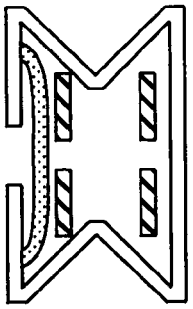
FIG. 24E
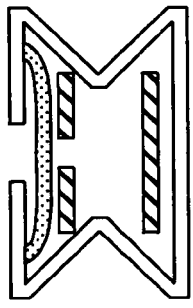
FIG. 24D
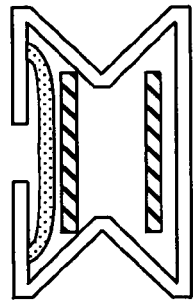
FIG. 24C
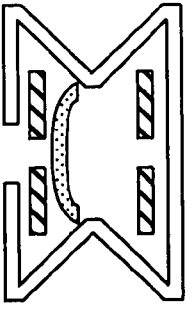
FIG. 24H
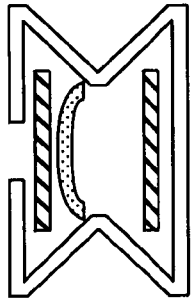
FIG. 24G
FIG. 24F

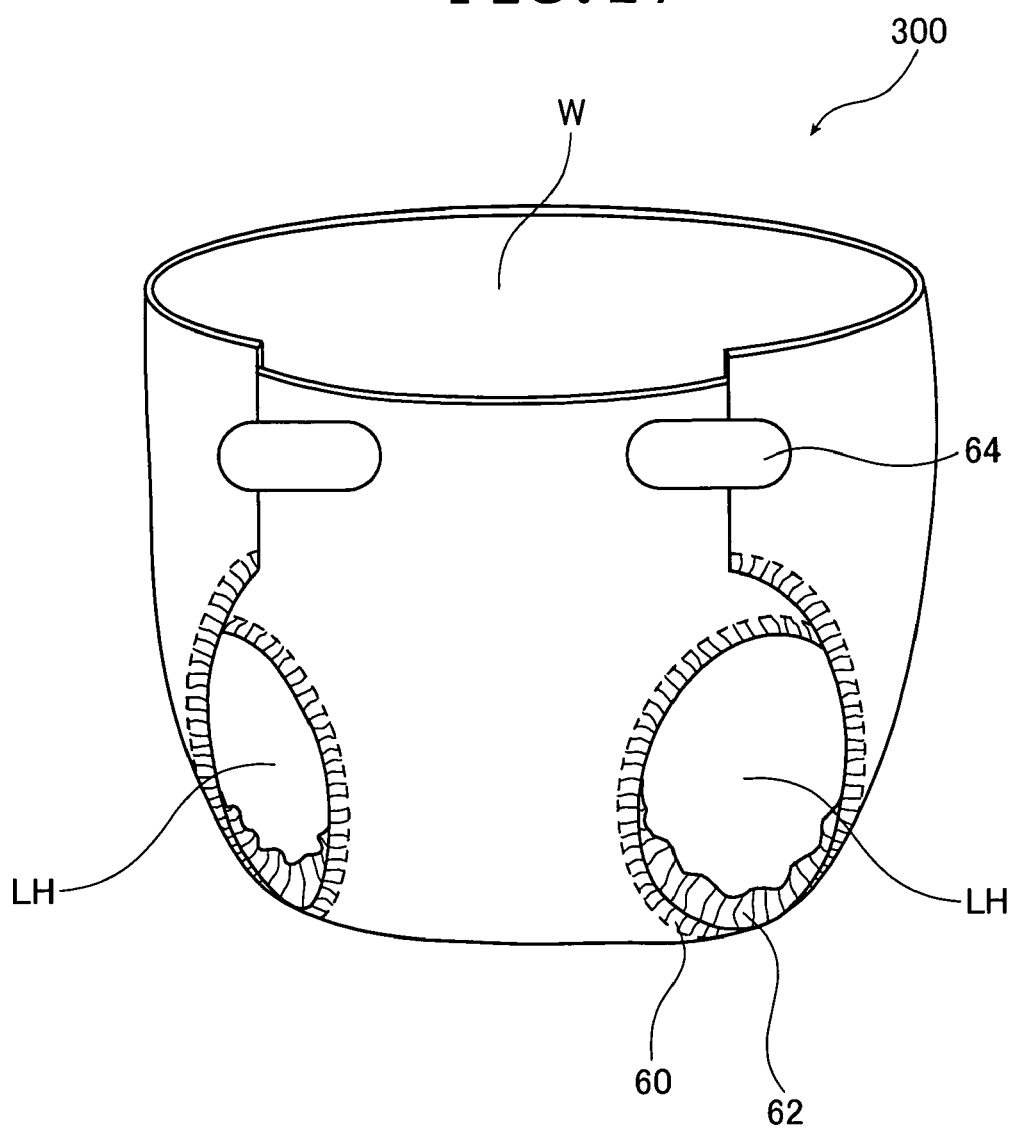

ABSORBENT ARTICLE

TECHNICAL FIELD

The present invention relates to a novel absorbent article.

BACKGROUND ART

An absorbent article such as a disposable diaper is an article for absorbing urine excreted from a wearer into an absorber employing an absorbing component such as wood pulp or a super absorbent polymer (hereinafter, may also be referred to as "SAP") and for receiving feces. A conventional absorbent article has no function of separating urine and feces, and thus urine and feces are liable to mix in use of the absorbent article. The mixing of urine and feces develops a problem of causing an offensive odor, a rash, or the like.

Correspondingly, various processes for separating urine and feces have been proposed.

For example, there is proposed a process for separating urine and feces by a partition member (see Patent Documents 1 and 2, for example).

Further, there is proposed a process for separating urine from feces by: providing an opening in a rear part of an absorbent article; and receiving the feces in the opening (see Patent Documents 2 to 5, for example).

Further, there is proposed a process for inhibiting contact between urine and feces by absorbing the urine rapidly to remove the urine from an inner surface of an absorbent article (see Patent Documents 6 and 7, for example).

Patent Document 1: JP 7-299092 A
Patent Document 2: WO 02/24130
Patent Document 3: JP 6-327715 A
Patent Document 4: JP 6-343660 A
Patent Document 5: JP 8-56986 A
Patent Document 6: JP 6-90977 A
Patent Document 7: JP 9-28732 A

DISCLOSURE OF THE INVENTION

Problems to be Solved by the Invention

However, the above-described conventional absorbent article is not capable of realizing efficient separation of urine and feces. Further, the conventional absorbent article has low urine absorption capacity and must be changed numerous times.

Therefore, it is an object of the present invention to provide an absorbent article capable of separating urine and feces efficiently in use and having high urine absorption capacity.

Means to Solve the Problems

The inventors of the present invention have conducted intensive studies for attaining the above-described object, and have completed an absorbent article having a novel structure.

That is, the present invention provides the following items (1) to (10).

(1) An absorbent article including:
a first sheet leak preventer;
a second sheet leak preventer present above and in a rear part of the first leak preventer; and
an absorber containing a super absorbent polymer, capable of absorbing a body fluid, and provided above the first leak preventer extending from a front part of the first leak preventer beneath the second leak preventer in at least one layer.

(2) The absorbent article according to the above item (1), in which a urine introduction part forming material is bonded to a part of a lower surface of a front end of the second leak preventer.

(3) The absorbent article according to the above item (1) or (2), further including a urine/feces stopping member in a front end or in a vicinity of the front end of the second leak preventer.

(4) The absorbent article according to any one of the above items (1) to (3), in which the absorber is separated and provided on right and left sides in a front part of the first leak preventer.

(5) The absorbent article according to any one of the above items (1) to (4), in which the absorber is separated and provided on right and left sides in a rear part of the first leak preventer.

(6) The absorbent article according to any one of the above items (1) to (5), in which a part or entire periphery of the first leak preventer rises upward.

(7) The absorbent article according to the above item (6), in which right and left side walls of the first leak preventer are folded inward.

(8) The absorbent article according to the above item (6) or (7), in which right and left side walls of the first leak preventer are formed into folded shape.

(9) The absorbent article according to the above item (8), in which the absorber is provided in each of at least two of two or more stepped-spaces defined by the right and left side walls of the first leak preventer formed into folded shape.

(10) The absorbent article according to any one of the above items (1) to (9), in which a part or entire periphery of the second leak preventer rises upward.

Effect of the Invention

The absorbent article of the present invention is capable of separating urine and feces efficiently in use and has high urine absorption capacity.

BRIEF DESCRIPTION OF DRAWINGS

FIG. 2 show schematic diagrams showing various shapes of a second leak preventer;

FIG. 12 show schematic diagrams showing various other examples of a urine/feces stopping member;

FIG. 23 show schematic diagrams showing various examples of positional relationship between a first leak preventer and a second leak preventer;

FIG. 24 show schematic diagrams showing various examples of positional relationship among a first leak preventer, a second leak preventer, and an absorbent;

FIG. 27 is a schematic diagram showing the absorbent article of the present invention according to the embodiment of a tape-type diaper;

Figure 1A:
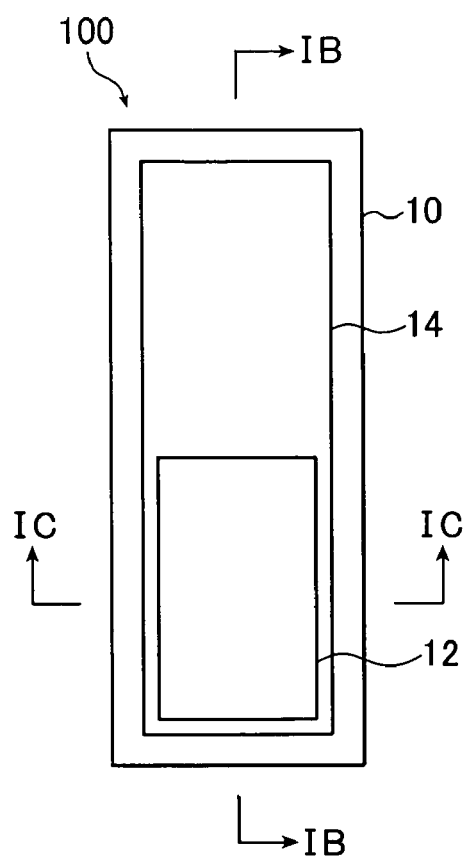
FIG. 1 show schematic diagrams each showing an example of an absorbent article of the present invention.

| Legend | |
|---|---|
| 10, 10a to 10e, 101, 102, 103 | FIRST LEAK PREVENTER |
| 12, 12a to 12r, 121, 122, 123 | SECOND LEAK PREVENTER |
| 13 | FECES DISPOSING SHEET |
| 14, 14a to 14g, 141, 142, 143 | ABSORBER |
| 16, 18, 20, 22, 24, 26, 27, 28 | URINE INTRODUCTION PART FORMING MEMBER |
| 17, 19, 21, 70 | BONDING PART |
| 30, 32, 34, 36, 38, 39, 40, 42a to 42m, 44a to 44d, 46a to 46e | URINE/FECES STOPPING MEMBER |
| 40a | URINE STOPPING PART |
| 40b | FECES STOPPING PART |
| 40c | BASE PART |
| 50 | SKIN CONTACT SHEET |
| 60 | OUTER GATHER |
| 61 | OUTER MEMBER |
| 62 | INNER GATHER |
| 64 | BONDING TAPE |
| 66 | WAIST GATHER |
| 68 | PERIPHERAL SHAPE RETAINING MEMBER |
| 72 | WAIST BAND |
| 74, 76 | REMOVABLE MEMBER |
| 80 | LIQUID GUIDE SHEET |
| 100, 110, 120, 130, 140, 150, 160, 170, 180, 190, 200, 210, 220, 230, 240, 250, 260, 270, 280, 300, 310, 320 | ABSORBENT ARTICLE |
| LH | LEG HOLE |
| W | WAIST HOLE |
| a | ANUS |
| m | URETHRAL OPENING |

BEST MODE FOR CARRYING OUT THE INVENTION

Hereinafter, an absorbent article of the present invention will be described in more detail based on preferable embodiment modes shown in attached drawings. In the specification of the present invention, when the absorbent article is actually worn, a side close to a skin of a wearer is referred to as an "upper" side and a side far therefrom is referred to as a "lower" side. In addition, when the absorbent article is actually worn, a side corresponding to a front side of a body of a wearer is referred to as "front" and a side corresponding to a rear side thereof is referred to as "rear". In the drawings, members which are actually in contact with each other may be shown to be separately positioned for easy understanding.

Figure 1B:
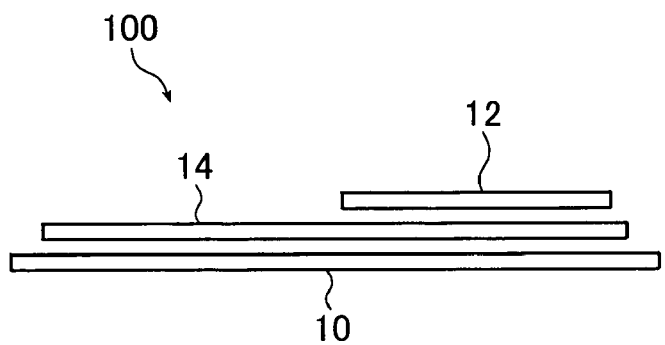
Figure 1C:
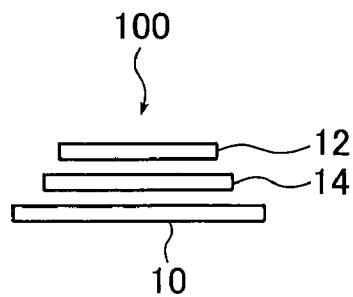

FIG. 1 are schematic diagrams each showing an example of the absorbent article of the present invention. FIG. 1(A) is a plan view. FIG. 1(B) is a longitudinal end view taken along the line IB-IB of FIG. 1(A), and FIG. 1(C) is a lateral end view taken along the line IC-IC of FIG. 1(A).

Note that, in each plan view of the attached drawings, a front side of an absorbent article or others is shown on an upper side of the diagram.

An absorbent article 100 of the present invention is basically provided with: a first leak preventer 10 in sheet form; a second leak preventer 12 in sheet form present above and in a rear part of the first leak preventer 10; and an absorber 14 containing a super absorbent polymer, capable of absorbing a body fluid, and provided above the first leak preventer 10 extending from a front part of the first leak preventer 10 beneath the second leak preventer 12 in at least one layer.

Materials generally used for a back sheet may be used as materials for the first leak preventer 10 and the second leak preventer 12. Specific examples of the materials that can be used include: a resin film of PE, PP, PET, EVA, or the like; and a body fluid impermeable sheet such as a foamed resin sheet made of the resin. Further, a sheet having gas permeability such as a gas permeable film is preferably used as the body fluid impermeable sheet.

The resin film may be used as a multilayer sheet of the film and a nonwoven fabric for the better touch or appearance. In this case, an SB nonwoven fabric, an SMS nonwoven fabric, a thermal bond nonwoven fabric, or the like having a relatively light weight is preferably used as the nonwoven fabric.

Further, a multilayer sheet of the resin film and a sheet absorber described below may be used.

Further, a highly water-resistant nonwoven fabric may be used. In this case, the highly water-resistant nonwoven fabric may be used alone, or used as a multilayer sheet of a film and the highly water-resistant nonwoven fabric.

The first leak preventer 10 and the second leak preventer 12 each may be formed of a plurality of members.

A longitudinal length, a longitudinal position, a lateral length, or the like of the second leak preventer is not particularly limited as long as the second leak preventer is capable of receiving feces.

A shape of the second leak preventer 12 is not particularly limited as long as the second leak preventer 12 has a shape of a sheet. For example, the second leak preventer 12 may have a shape shown in FIG. 2.

FIG. 2 are schematic diagrams showing various shapes of the second leak preventer. FIGS. 2(A) to 2(J) are each a plan view.

The absorber 14 used in the present invention is not particularly limited as long as it may absorb a body fluid. For example, a powdery absorber such as powdery wood pulp or unprocessed SAP may be used as the absorber 14, but the absorber 14 is preferably a sheet absorber in consideration of shape stability, possibility of falling, and the like.

The sheet absorber is preferably a super absorbent sheet containing 50 wt % or more SAP, preferably 60 to 95 wt % SAP.

The super absorbent sheet is an ultrathin sheet absorber containing SAP as a main component. The super absorbent sheet has a very high SAP content, and thus is very thin. The super absorbent sheet has a thickness of preferably 1.5 mm or less, more preferably 1 mm or less.

A structure or a production process for the super absorbent sheet is not particularly limited as long as the super absorbent sheet is an ultrathin sheet absorber containing SAP as a main component.

An example of the super absorbent sheet includes a super absorbent sheet obtained through an Air Laid process. The Air Laid process involves mixing pulverized wood pulp and SAP, adding a binder, and forming the mixture into a sheet, to thereby obtain a super absorbent sheet. Examples of the super absorbent sheet obtained through this process include: NOVATHIN (US trade name) available from Reyonier Inc.; and B-SAP available From Oji Kinocloth Co., Ltd.

Another example of the super absorbent sheet includes a super absorbent sheet obtained through a process involving coating SAP-dispersed slurry on a body fluid permeable sheet such as a nonwoven fabric. The SAP-dispersed slurry is preferably prepared by dispersing SAP and microfibrillated cellulose (MFC) in a mixed solvent of water and ethanol. An example of the super absorbent sheet obtained through this process includes MegaThin (trade name) available from Japan Absorbent Technology Institute.

Other examples of the super absorbent sheet include: a super absorbent sheet obtained through a process involving carrying a large amount of SAP on a raised nonwoven fabric and fixing the SAP with a hot melt binder, an emulsion binder, an aqueous fiber, or the like; a super absorbent sheet obtained through a process involving mixing fibrous SAP with a PET (polyethylene terephthalate) fiber and forming the mixture into a web; and an SAP sheet obtained by providing tissues above and below an SAP layer.

The absorber 14 is provided above the first leak preventer 10 extending from a front part of the first leak preventer 10 beneath the second leak preventer 12 in at least one layer. That is, the absorber 14 may be provided as one layer, or as two or more layers (multilayer).

Further, the absorber 14 may be provided while being folded.

Next, a mechanism of the absorbent article 100 will be described.

Figure 3:
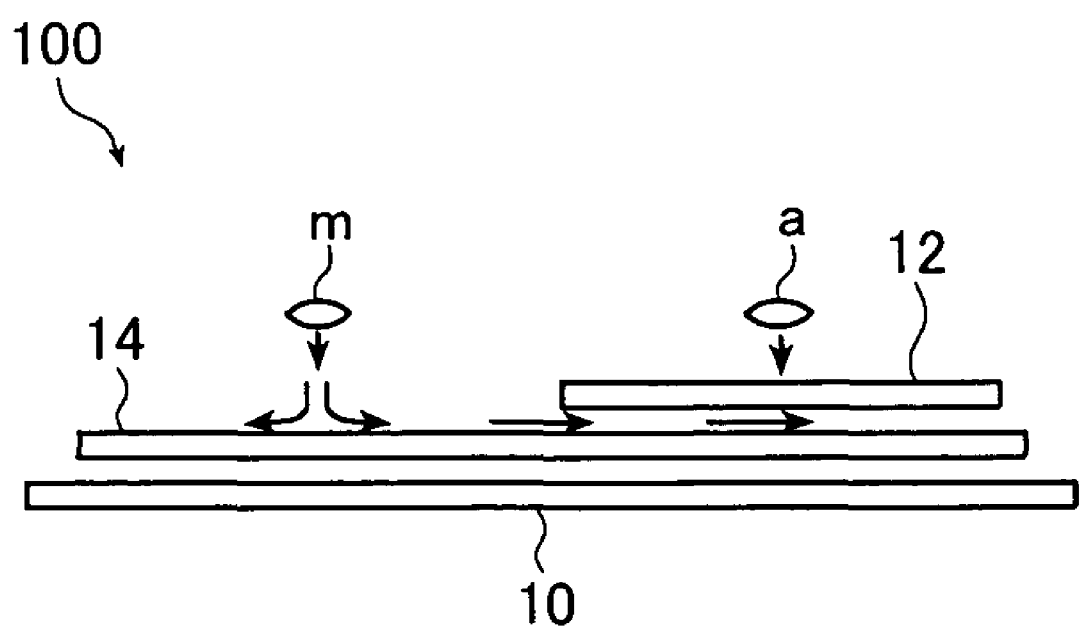
FIG. 3 is a schematic diagram illustrating a mechanism of an absorbent article of the present invention.

FIG. 3 is a schematic diagram illustrating a mechanism of the absorbent article of the present invention. FIG. 3 shows a longitudinal sectional view of the absorbent article.

The absorbent article 100 is worn such that a urethral opening m of a wearer is positioned above the first leak preventer 10, and an anus a thereof is positioned above the second leak preventer 12.

Urine excreted from the urethral opening m of the wearer to an upper side of the absorber 14 present in an upper part of the first leak preventer 10 diffuses across the entire absorber 14 while being absorbed therein, as shown by arrows in FIG. 3.

Meanwhile, feces excreted from the anus a of the wearer to the second leak preventer 12 is received by the second leak preventer 12.

The absorbent article 100 of the present invention receives the urine by the absorber 14 present above the first leak preventer 10 and receives the feces by the second leak preventer 12. Thus, the urine and the feces are not brought into contact with each other unless the urine flows over to the second leak preventer 12 or the feces flows over to the absorber 14.

In the absorbent article 100 of the present invention, the absorber 14 is provided above the first leak preventer 10 extending from a front part thereof beneath the second leak preventer 12. Thus, a urine absorption amount significantly increases compared with that of a conventional way, in which urine and feces are separated by a partition member and the urine is absorbed in a front part alone.

Hereinafter, the absorbent article of the present invention will be described in more detail by referring to other preferable modes.

Figure 4A:
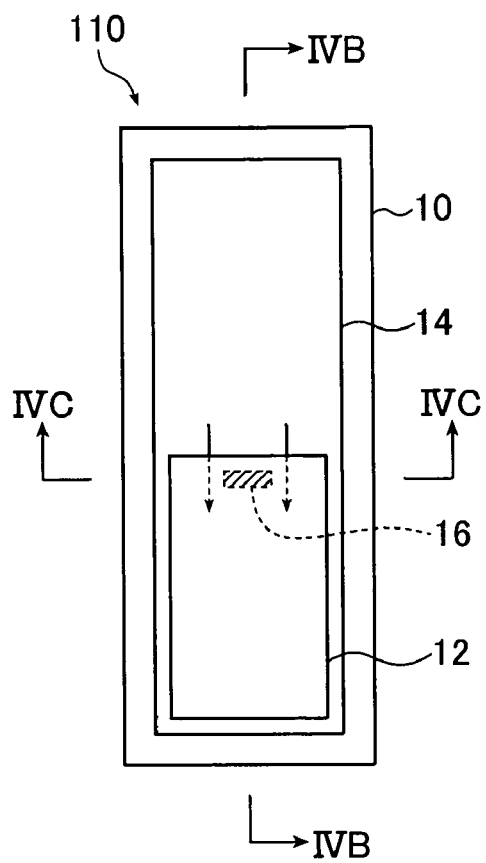
FIG. 4 show schematic diagrams each showing another example of the absorbent article of the present invention.
Figure 4B:
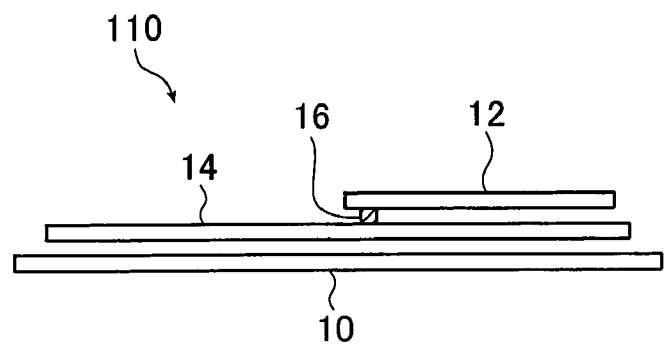
Figure 4C:
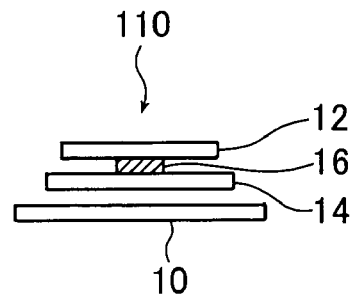

FIG. 4 are schematic diagrams each showing another example of the absorbent article of the present invention. FIG. 4(A) is a plan view. FIG. 4(B) is a longitudinal end view taken along the line IVB-IVB of FIG. 4(A), and FIG. 4(C) is a lateral end view taken along the line IVC-IVC of FIG. 4(A).

An absorbent article 110 shown in FIG. 4 is basically the same as the absorbent article 100, but differs in that a lower surface of a front end of the second leak preventer 12 is partly bonded to an upper surface of the absorber 14 at a lateral center part of the absorbent article 110 through a urine introduction part forming member 16.

In order to transfer the excreted urine smoothly to the absorber 14 present under the second leak preventer 12, preferably, a gap is provided and secured between the second leak preventer 12 and the absorber 14, particularly in a vicinity of the front end of the second leak preventer 12.

In the absorbent article 110, the urine introduction part forming member 16 is provided between the lower surface of the front end of the second leak preventer 12 and the upper surface of the absorber 14, to thereby assure the gap between the second leak preventer 12 and the absorber 14. The urine transferred to a lower side of the second leak preventer 12 is divided into right and left directions by the urine introduction part forming member 16 and rectified for smooth transfer. Further, the second leak preventer 12 and the absorber 14 are bonded through the urine introduction part forming member 16, and a positional relationship among the second leak preventer 12, the absorber 14, and the urine introduction forming member 16 is maintained substantially constant. The urine introduction part forming member 16 only needs to be bonded to the second leak prevent 12, and needs not be bonded to the absorber 14.

The urine introduction part 16 must have a certain thickness for assuring a gap between the second leak preventer 12 and the absorber 14, but is not particularly limited otherwise. Examples of a material for the urine introduction part forming member 16 include an adhesive, rubber, a film, foam (a foamed product), and a bulky nonwoven fabric. In a case where the material therefor is an adhesive, the adhesive is applied so as to have a certain thickness. In a case where the material therefor is rubber, a film, a foamed product, or a bulky nonwoven fabric, the material is formed into a thin piece or a strip, and a surface thereof and the surface of the second leak preventer 12 are bonded through an adhesive or the like.

The urine introduction part forming member 16 refers to a member prepared by: providing a urethane foam block having a length (longitudinal length) of 10 mm, a width (lateral length) of 20 mm, and a thickness of 3 mm between a lower surface of a front end of the second leak preventer 12 and an upper surface of the absorber 14 and being fixed by a hot melt adhesive.

In the absorbent article 110, the urine passes through both sides of the urine introduction part forming member 16 and transfers to a rear part of the absorber 14, as shown by arrows in FIG. 4(A). This is because urethane foam used for the urine introduction part forming member 16 has no liquid permeability. In this way, a passage of the urine is restricted to a certain extent, and thus a large amount of urine converges and flows through specific positions, to thereby facilitate transfer of the urine to the rear part of the absorber 14.

Figure 5A:
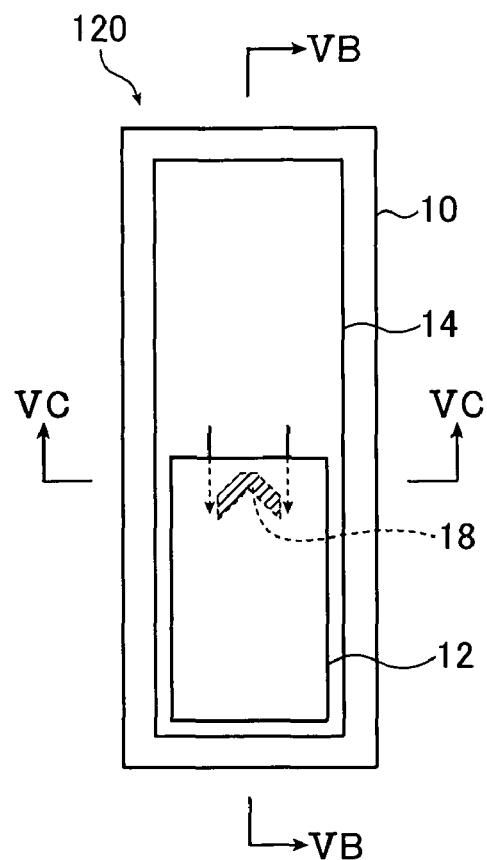
FIG. 5 show schematic diagrams each showing still another example of the absorbent article of the present invention.
Figure 5B:
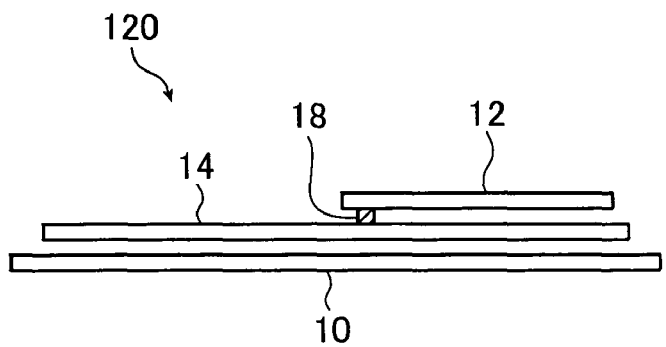
Figure 5C:
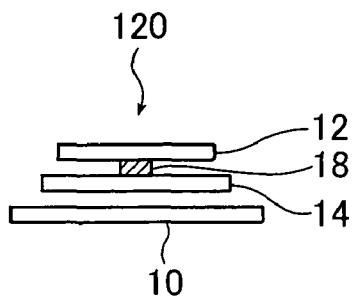

FIG. 5 are schematic diagrams each showing still another example of the absorbent article of the present invention. FIG. 5(A) is a plan view. FIG. 5(B) is a longitudinal end view taken along the line VB-VB of FIG. 5(A), and FIG. 5(C) is a lateral end view taken along the line VC-VC of FIG. 5(A).

An absorbent article 120 shown in FIG. 5 is basically the same as the absorbent article 110 in structure and function, but differs in shape of the urine introduction part forming member. The urine introduction part forming member 16 is laterally linear, but a urine introduction part forming member 18 has a V-shape with an apex on a front side, to thereby accelerate smooth transfer of the urine from the front part to rear part of the absorber 14 and prevent efficiently back flow of the urine from the rear part to front part of the absorber 14.

Figure 6A:
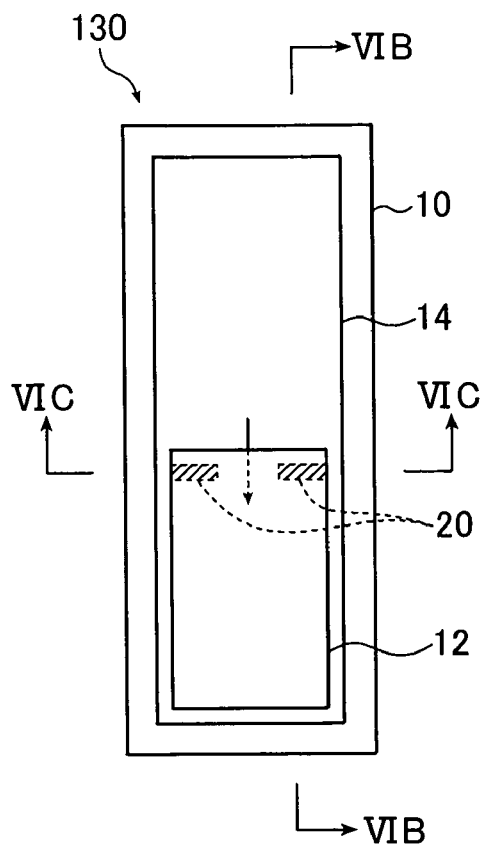
FIG. 6 show schematic diagrams each showing yet another example of the absorbent article of the present invention.
Figure 6B:
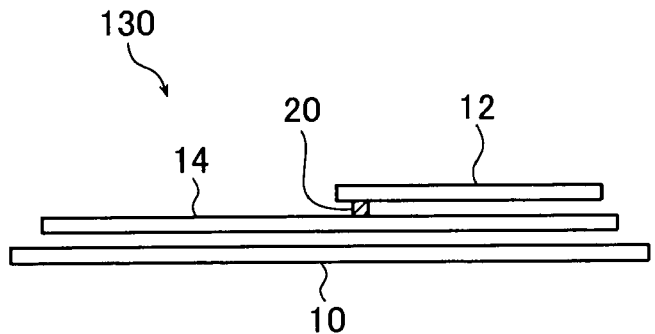
Figure 6C:
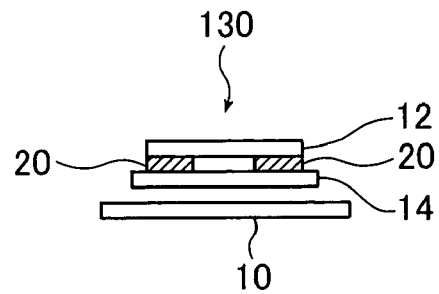

FIG. 6 are schematic diagrams each showing yet another example of the absorbent article of the present invention. FIG. 6(A) is a plan view. FIG. 6(B) is a longitudinal end view taken along the line VIB-VIB of FIG. 6(A), and FIG. 6(C) is a lateral end view taken along the line VIC-VIC of FIG. 6(A).

An absorbent article 130 shown in FIG. 6 is basically the same as the absorbent article 110 in structure and function, but differs in position of the urine introduction part forming member. A urine introduction part forming member 20 is separated and positioned on right and left sides.

Figure 7A:
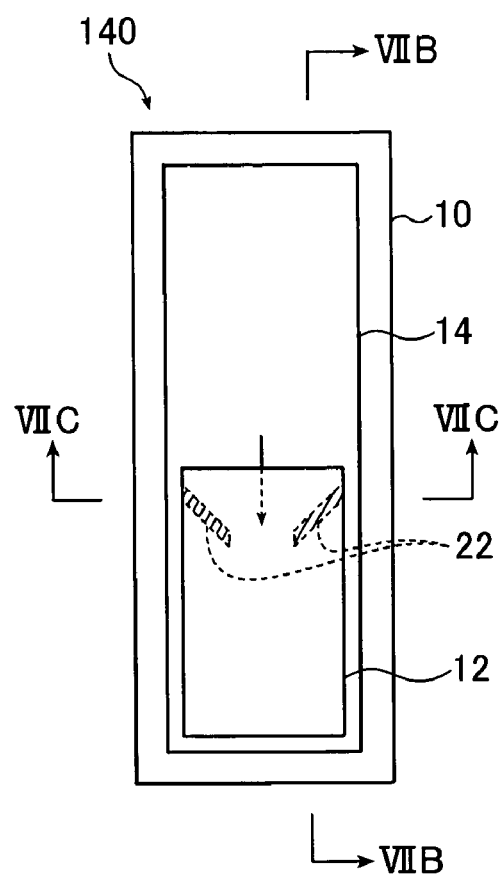
FIG. 7 show schematic diagrams each showing still yet another example of the absorbent article of the present invention.
Figure 7B:
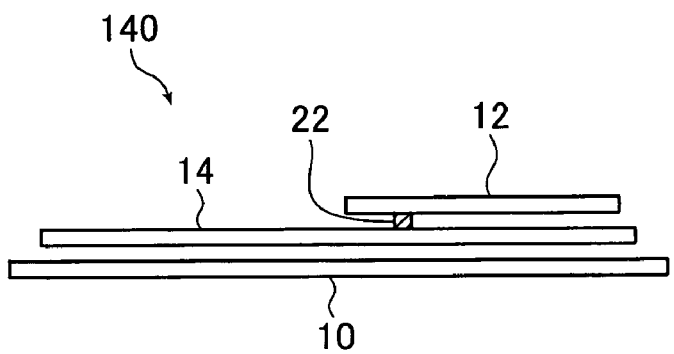
Figure 7C:
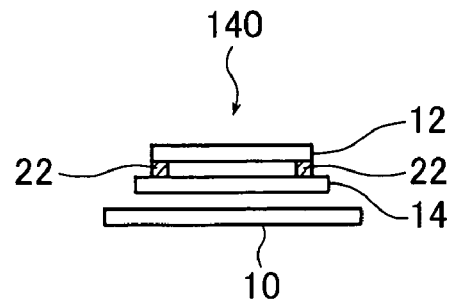

FIG. 7 are schematic diagrams each showing still yet another example of the absorbent article of the present invention. FIG. 7(A) is a plan view. FIG. 7(B) is a longitudinal end view taken along the line VIIB-VIIB of FIG. 7(A), and FIG. 7(C) is a lateral end view taken along the line VIIC-VIIC of FIG. 7(A).

An absorbent article 140 shown in FIG. 7 is basically the same as the absorbent article 130 in structure and function, but differs in shape of the urine introduction part forming member. A urine introduction forming member 22 is separated into right and left parts such that outer sides thereof are provided frontward, and inner sides thereof provided rearward. Such a shape of the urine introduction forming member 22 converges the urine to a center part, to thereby accelerate smooth transfer of the urine from the front part to rear part of the absorber 14 and prevent efficiently back flow of the urine from the rear part to front part of the absorber 14.

Figure 8A:
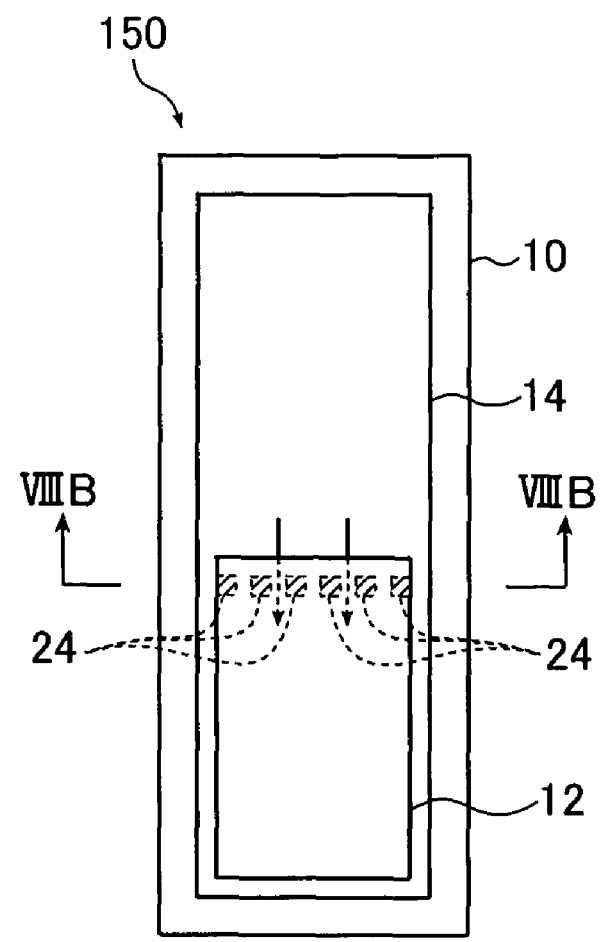
FIG. 8 show schematic diagrams each showing an example of the absorbent article of the present invention.
Figure 8B:
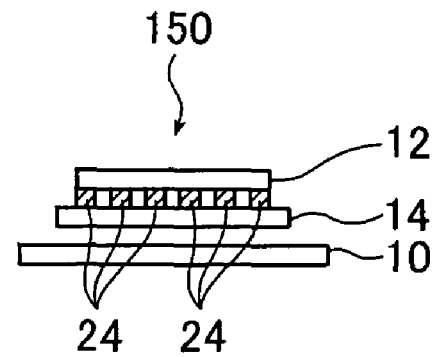

FIG. 8 are schematic diagrams each showing an example of the absorbent article of the present invention. FIG. 8(A) is a plan view, and FIG. 8(B) is a lateral end view taken along the line VIIIB-VIIIB of FIG. 8(A).

An absorbent article 150 shown in FIG. 8 is basically the same as the absorbent article 100, but differs in that a lower surface of a front end of the second leak preventer 12 is partly bonded to an upper surface of the absorber 14 across an entire lateral length through a urine introduction part forming member 24 having a plurality of honeycomb pores. The second leak preventer 12 and the urine introduction part forming member 24 are bonded through an adhesive or the like, and the absorber 14 and the urine introduction part forming member 24 are bonded through an adhesive or the like.

In the absorbent article 150, the urine passes through the urine introduction part forming member 24 and transfers to a rear part of the absorber 14, as shown by arrows in FIG. 8(A). Flow of the urine is divided by the urine introduction part forming member 24 and rectified, to thereby prevent very efficiently back flow of the urine from the rear part to front part of the absorber 14.

Figure 9A:
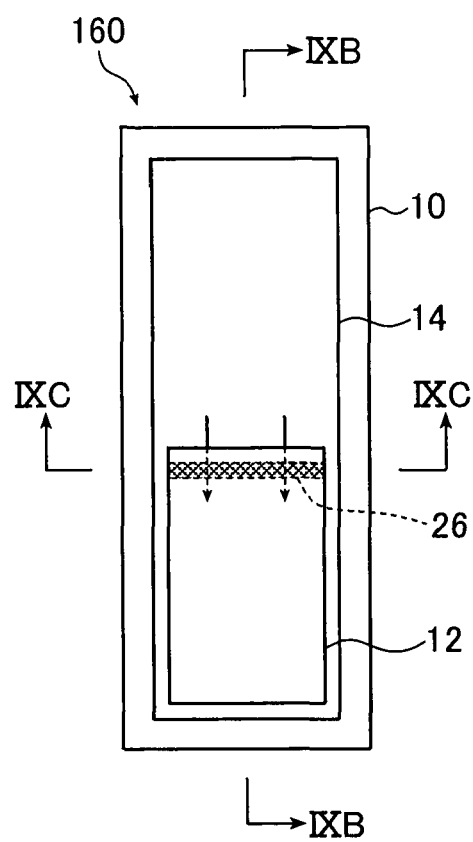
FIG. 9 show schematic diagrams each showing another example of the present invention.
Figure 9B:
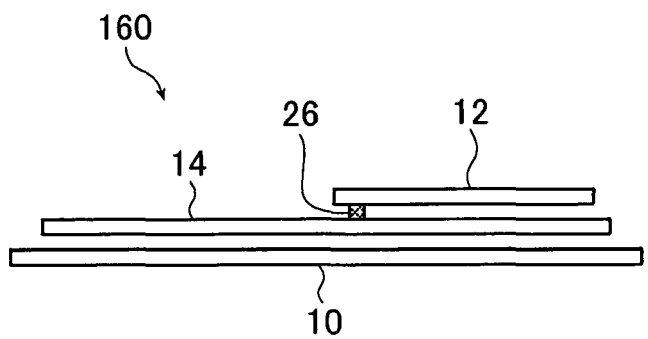
Figure 9C:
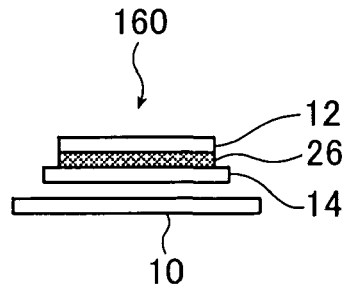

FIG. 9 are schematic diagrams each showing another example of the absorbent article of the present invention. FIG. 9(A) is a plan view. FIG. 9(B) is a longitudinal end view taken along the line IXB-IXB of FIG. 9(A), and FIG. 9(C) is a lateral end view taken along the line IXC-IXC of FIG. 9(A).

An absorbent article 160 shown in FIG. 9 is basically the same as the absorbent article 100, but differs in that a lower surface of a front end of the second leak preventer 12 is partly bonded to an upper surface of the absorber 14 across an entire lateral length through a urine introduction part forming member 26 having liquid permeability. The second leak preventer 12 and the urine introduction part forming member 26 are bonded through an adhesive or the like, and the absorber 14 and the urine introduction part forming member 26 are bonded through an adhesive or the like.

The urine introduction part forming member 26 having liquid permeability is not particularly limited as long as it has liquid permeability. Examples thereof that can be used include: a nonwoven fabric of a synthetic fiber such as a PP nonwoven fabric, a PET nonwoven fabric, or a PE nonwoven fabric; a net filter (Moltofilter, available from Inoac Corporation, for example); a sheet piece such as high expansion foam having open cells. The nonwoven fabric preferably has bulky and thick fibers for excellent cushioning property and liquid permeability.

In the absorbent article 160, the urine passes through the urine introduction part forming member 26 having liquid permeability and transfers to a rear part of the absorber 14, as shown by arrows in FIG. 9(A).

FIG. 10 are schematic diagrams each showing still another example of the absorbent article of the present invention. FIG.

Figure 10A:
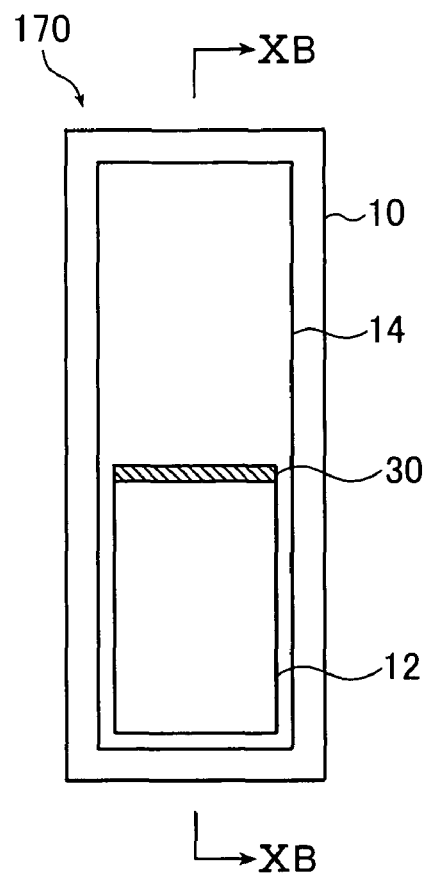
FIG. 10 show schematic diagrams each showing still another example of the absorbent article of the present invention.
Figure 10B:
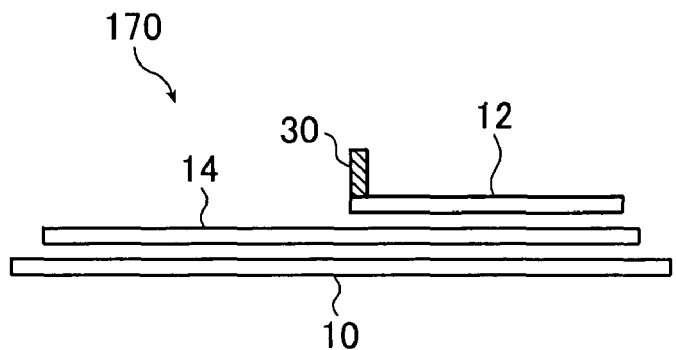

10(A) is a plan view, and FIG. 10(B) is a longitudinal end view taken along the line XB-XB of FIG. 10(A).

An absorbent article 170 shown in FIG. 10 includes a urine/feces stopping member 30 on a front end of the second leak preventer 12.

The urine/feces stopping member has a function of holding urine in the first leak preventer and/or a function of holding feces in the second leak preventer, to thereby prevent contact between the urine and the feces or prevent leak of the urine and/or the feces.

A material for the urine/feces stopping member 30 is not particularly limited, but the urine/feces stopping member 30 is preferably liquid impermeable as a whole. Examples of the material therefor include: a foamed product (made of PU, PP, or PP/EVA, for example); a material including as a core a foamed product covered with a hydrophilic material; and a material including as a core a foamed product covered with a hydrophilic material and further covered with a nonwoven fabric or body fluid impermeable sheet. The second leak preventer 12 may extend to form the urine/feces stopping member.

FIG. 11 are schematic diagrams showing various examples of the urine/feces stopping member. FIGS. 11(A) to 11(C) and 11(E) are each a longitudinal end view, and FIG. 11(D) is a plan view.

Figure 11A:
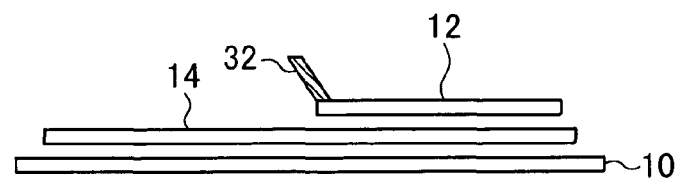
FIG. 11 show schematic diagrams showing various examples of a urine/feces stopping member.

A urine/feces stopping member 32 shown in FIG. 11(A) is provided such that an upper end of the urine/feces stopping member 32 is positioned frontward at a front end of the second leak preventer 12. In this way, urine is particularly efficiently prevented from entering into the second leak preventer 12.

Figure 11B:
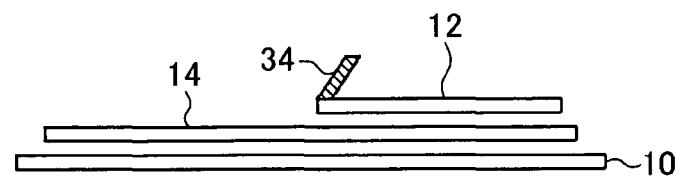

A urine/feces stopping member 34 shown in FIG. 11(B) is provided such that an upper end of the urine/feces stopping member 34 is positioned rearward at a front end of the second leak preventer 12. In this way, feces are particularly efficiently prevented from leaking from the second leak preventer 12.

Figure 11C:
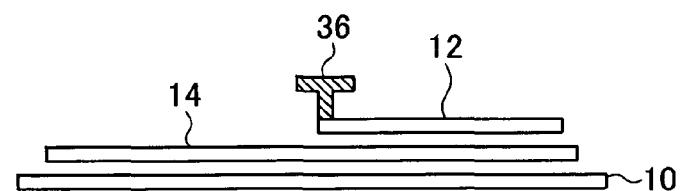

A urine/feces stopping member 36 shown in FIG. 11(C) has a T-shape. In this way, urine is particularly efficiently prevented from entering into the second leak preventer 12 and feces are particularly efficiently prevented from leaking from the second leak preventer 12.

Figure 11D:
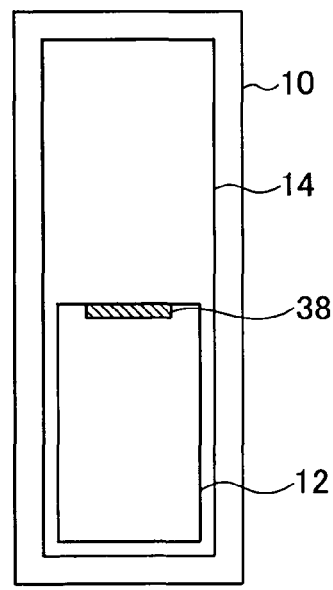

The urine/feces stopping member is generally provided across an entire lateral width of the absorbent article. However, a urine/feces stopping member 38 shown in FIG. 11(D) is partly provided at a center part of a front end of the second leak preventer 12. This embodiment mode is for preventing contact between urine and feces at a lateral center part where the urine and the feces are liable to contact each other.

Figure 11E:
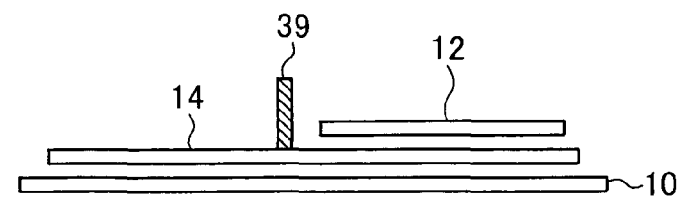

A urine/feces stopping member 39 shown in FIG. 11(E) is provided on a surface of the absorber 14 at a distance of about 2 to 3 cm in front of the second leak preventer 12. In this way, even if urine flows over the urine/feces stopping member 39 to a rear side, the urine is absorbed by the absorber 14 present between the urine/feces stopping member 39 and the second leak preventer 12. Thus, the urine is efficiently prevented from flowing over the second leak preventer 12.

The urine/feces stopping members 30, 32, 34, and 36 each may have the structure of the urine/feces stopping member 38.

A shape of the urine/feces stopping member is not particularly limited. In addition to the shapes as described above, the urine/feces stopping member may have the shapes shown in FIGS. 12 to 14.

FIGS. 12 to 14 are schematic diagrams showing various examples of the urine/feces stopping member. FIGS. 12(A) to 12(M) are each a plan view, and FIGS. 13(A) to 13(D) are each a side view. FIGS. 14(A) to 14(E) are each a lateral end view. In FIGS. 12 to 14, reference symbols 12a to 12m each represent a second leak preventer, and reference symbol 27 represents a urine introduction part forming member having liquid permeability. Reference symbols 42a to 42m, 44a to 44d, and 46a to 46e each represent a urine/feces stopping member.

Figure 13A:
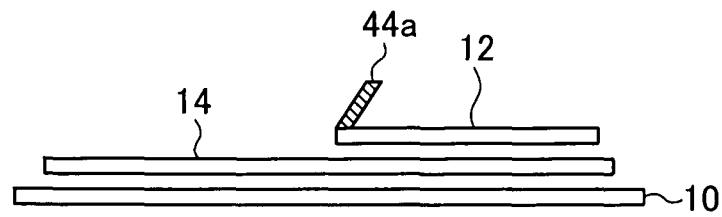
FIG. 13 show schematic diagrams showing various still other examples of a urine/feces stopping member.
Figure 13B:
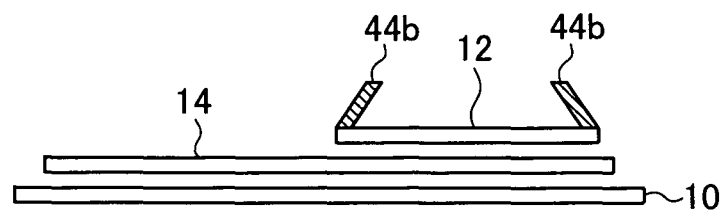
Figure 13C:
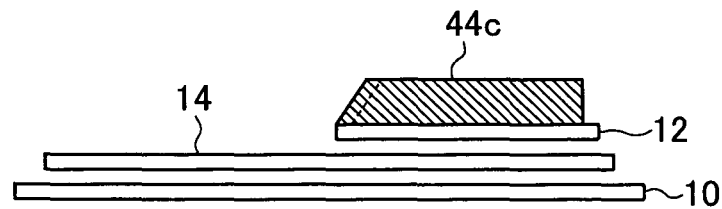
Figure 13D:
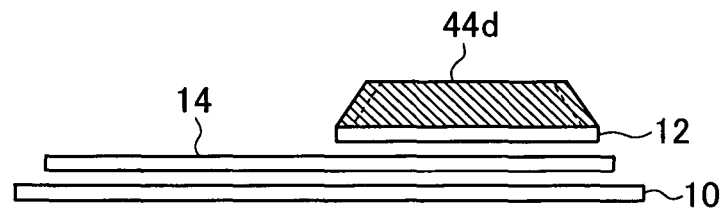
Figure 14A:
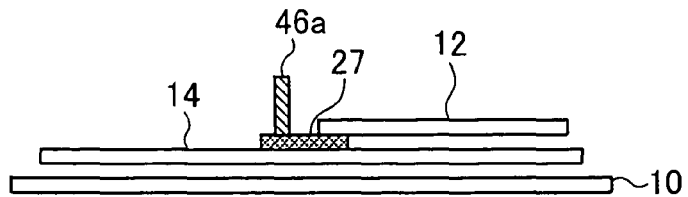
FIG. 14 show schematic diagrams showing various yet other examples of a urine/feces stopping member.
Figure 14B:
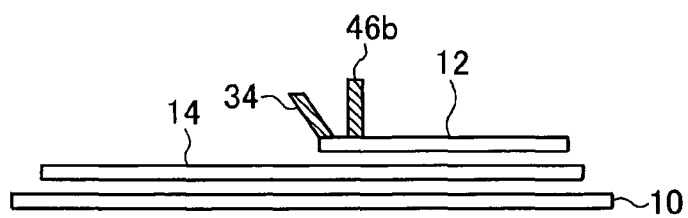
Figure 14C:
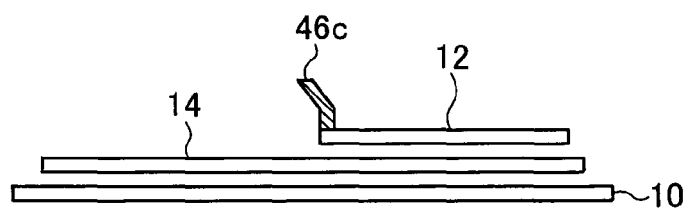
Figure 14D:
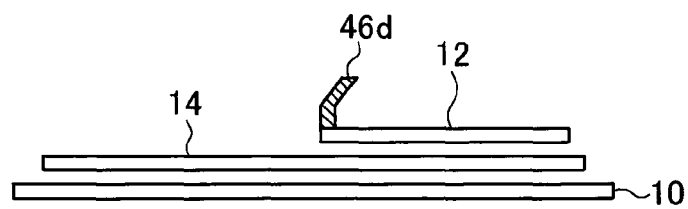
Figure 14E:
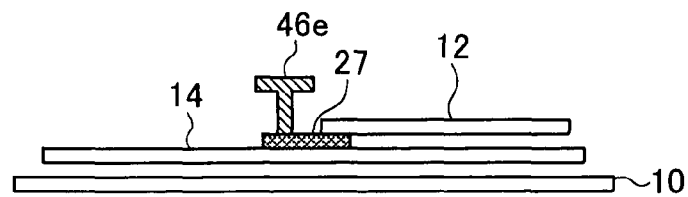

Note that, FIGS. 13(C) and 13(D) each show a case where urine/feces stopping members are provided on both right and left sides of the second preventer 12 of each of FIGS. 13(A) and 13(B).

FIG. 15 are schematic diagrams showing various examples of a position of an absorber. FIGS. 15(A) to 15(F) are each a plan view.

The absorber 14 shown in FIG. 1 is provided substantially across the entire lateral width of the first leak preventer 10. In this case, an amount of the absorber is large, increasing a urine absorption amount.

Figure 15A:
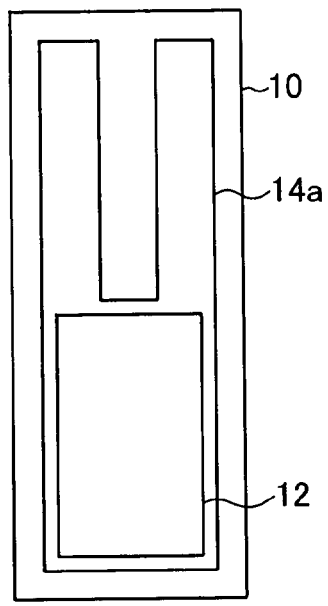
FIG. 15 show schematic diagrams showing various examples of a position of an absorber.

An absorber 14a shown in FIG. 15(A) is separated and provided on right and left sides of the first leak preventer 10 in its front part, and is provided substantially across the entire lateral width of the first leak preventer 10 in its rear part. In this case, in initial absorption, a front part of the absorber 14a mainly absorbs urine and swells, to thereby form a depressed part at a lateral center part. Then, when the urine is further excreted, the depressed part serves as a passage to accelerate transfer of the urine to a rear part of the absorber 14a, to thereby provide excellent usability in the rear part of the absorber 14a.

Figure 15B:
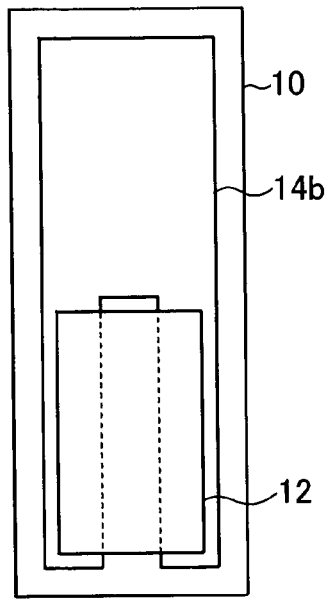

An absorber 14b shown in FIG. 15(B) is provided substantially across the entire lateral width in a front part of the first leak preventer 10, and is separated and provided on right and left sides of the first leak preventer 10 on its rear part. In this case, a rear part of the absorber 14b absorbs urine and swells, to thereby form a depressed part at a lateral center part. In this way, the second leak preventer 12 sags down at a lateral center part, to thereby increase an amount of feces to be received.

In this embodiment mode, a lower surface of a front end of the second leak preventer 12 may be partly bonded to an upper surface of the first leak preventer 10. In FIG. 15(F), a lower surface of a front end of the second leak preventer 12 is partly bonded to an upper surface of the first leak preventer 10 through a bonding part 17. This embodiment mode has a space formed for receiving feces from initial use.

A front end of the bonding part 17 is preferably at a position 0 to 40 mm behind the front end of the second leak preventer 12, and a rear end thereof is preferably at a position between 20 mm behind the front end of the second leak preventer 12 and the position of the rear end of the second leak preventer 12.

The bonding part 17 preferably has a lateral length of 2 to 20 mm.

The position and size of the bonding part 17 within the above ranges do not suppress swelling of the absorber, and thus a large urine absorption amount can be maintained.

Figure 15C:
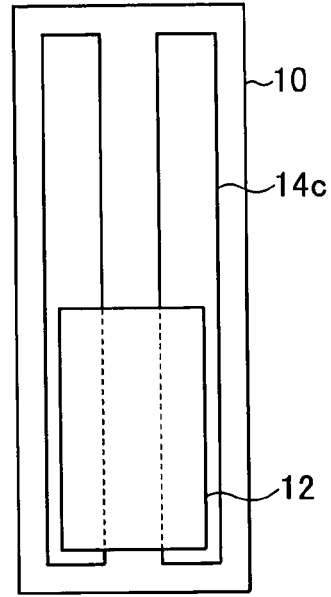

An absorber 14c shown in FIG. 15(C) is provided so as to be separated to right and left sides of the first leak preventer 10 from its front part to its rear part. This case provides both effects of the above-described absorbers 14a and 14b.

Figure 15D:
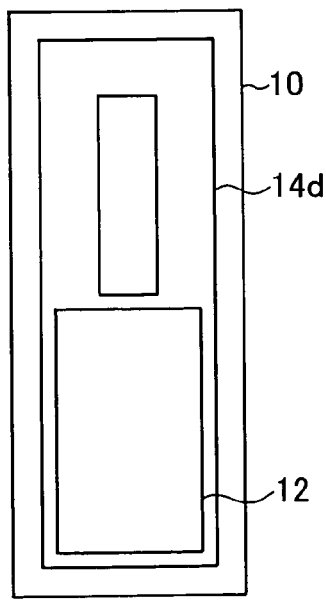

An absorber 14d shown in FIG. 15(D) is basically the same as the absorber 14a, but differs in that right and left parts of the absorber 14d are bonded at its front end. This case provides substantially the same effects as those of the above-described absorber 14a.

Figure 15E:
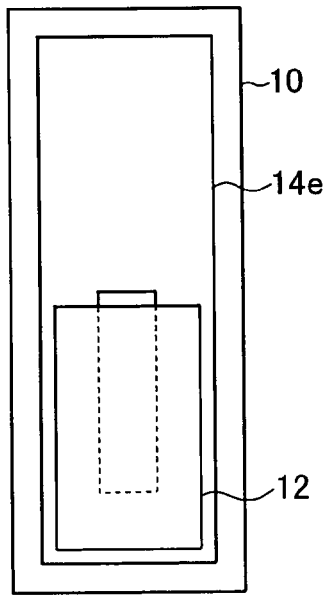
Figure 15F:
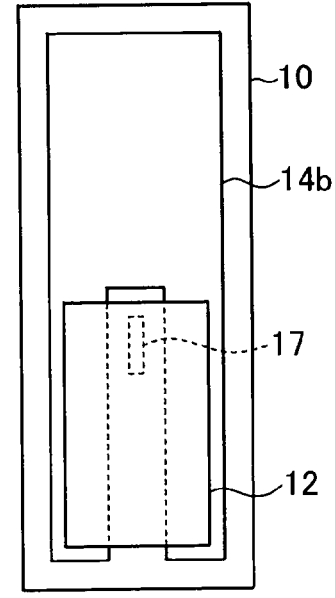

An absorber 14e shown in FIG. 15(E) is basically the same as the absorber 14b, but differs in that right and left parts of the absorber 14e are bonded at its rear end. This case provides substantially the same effects as those of the above-described absorber 14b.

FIG. 16 are schematic diagrams each showing yet another example of the absorbent article of the present invention. FIG. 16(A) is a plan view, and FIG. 16(B) is a lateral end view taken along the line XVIB-XVIB of FIG. 16(A). FIGS. 16(C) and 16(D) are each a lateral end view of the absorbent article according to another embodiment mode of the present invention.

Figure 16A:
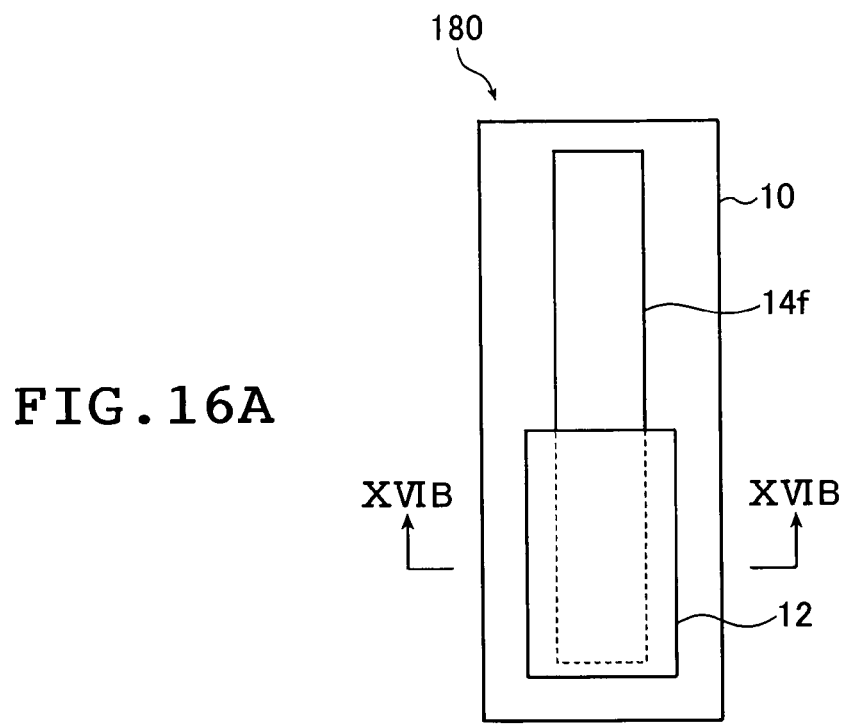
FIG. 16 show schematic diagrams each showing yet another example of the absorbent article of the present invention.
Figure 16B:
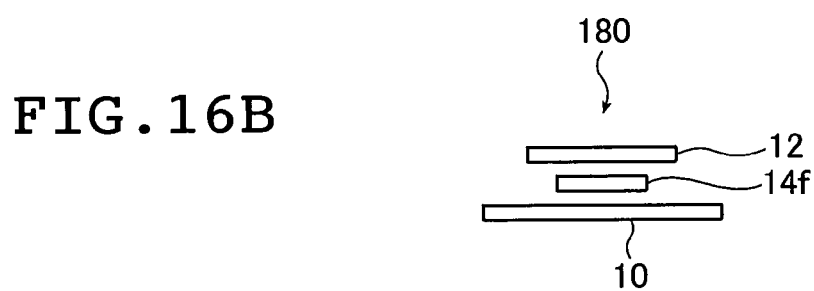

In an absorbent article 180 shown in FIGS. 16(A) and 16(B), a lateral length of an absorber 14f is shorter than a lateral length of the second leak preventer 12.

Figure 16C:
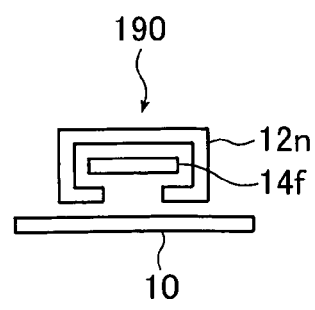

An absorbent article 190 shown in FIG. 16(C) is basically the same as the absorbent article 180, but differs in that: both right and left sides of a second leak preventer 12n come down to form side walls; and the side walls are folded inward to surround the absorber 14f.

Figure 16D:
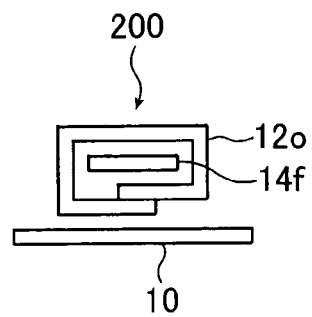

An absorbent article 200 shown in FIG. 16(D) is basically the same as the absorbent article 190, but differs in that ends of side walls of a second leak preventer 12o overlap to completely surround the absorber 14f.

A part or entire periphery of the first leak preventer preferably rises upward.

Figure 17A:
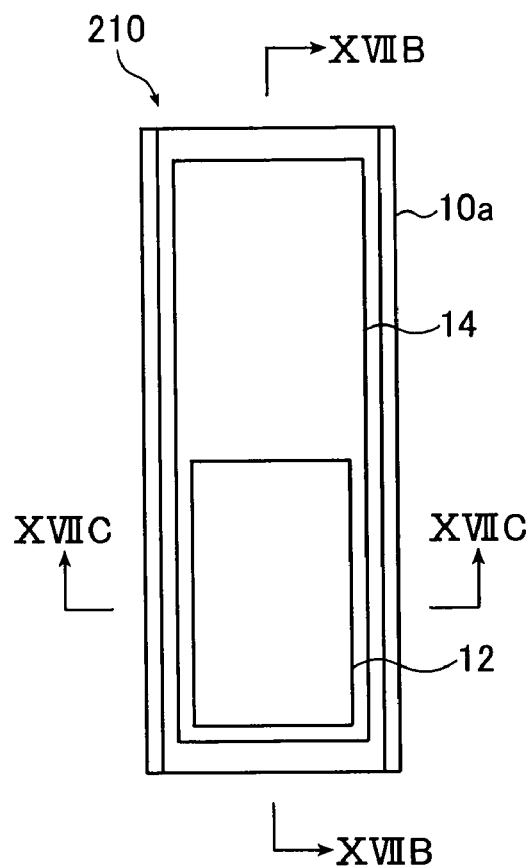
FIG. 17 show schematic diagrams each showing still yet another example of the absorbent article of the present invention.
Figure 17B:
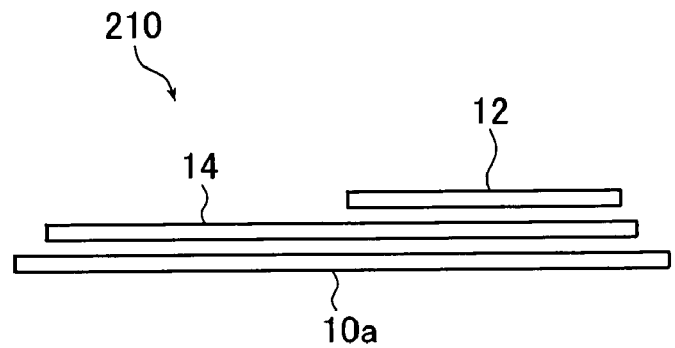
Figure 17C:
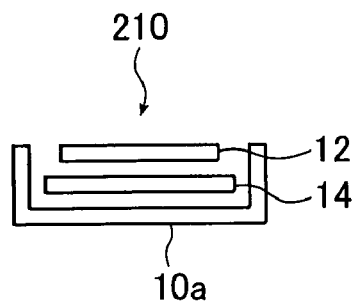

FIG. 17 are schematic diagrams each showing still another example of the absorbent article of the present invention. FIG. 17(A) is a plan view. FIG. 17(B) is a longitudinal end view taken along the line XVIIB-XVIIB of FIG. 17(A), and FIG. 17(C) is a lateral end view taken along the line XVIIC-XVIIC of FIG. 17(A).

In an absorbent article 210 shown in FIG. 17, both right and left sides of a first leak preventer 10a rise upward. In this way, urine hardly leaks from the right and left sides of the first leak preventer 10a.

Figure 18A:
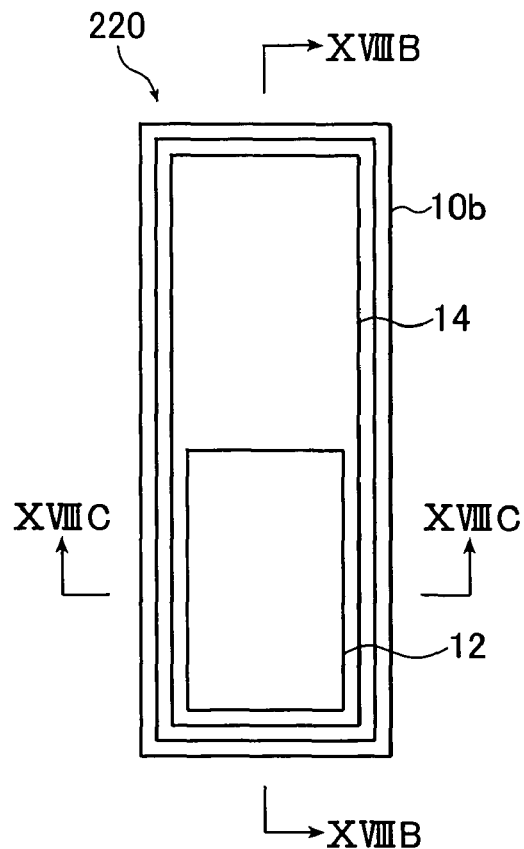
FIG. 18 show schematic diagrams each showing an example of the absorbent article of the present invention.
Figure 18B:
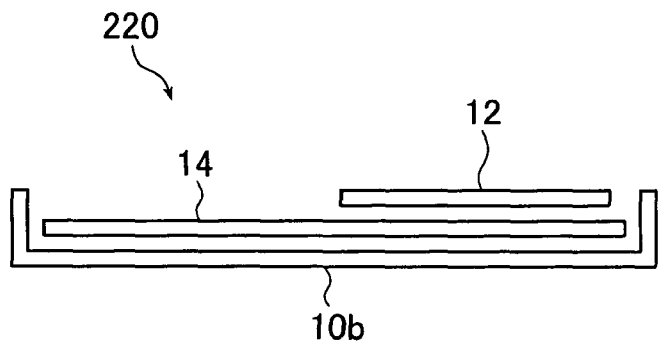
Figure 18C:
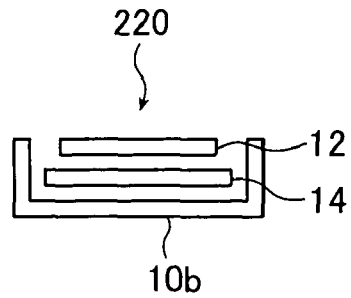

FIG. 18 are schematic diagrams each showing an example of the absorbent article of the present invention. FIG. 18(A) is a plan view. FIG. 18(B) is a longitudinal end view taken along the line XVIIIB-XVIIIB of FIG. 18(A), and FIG. 18(C) is a lateral end view taken along the line XVIIIC-XVIIIC of FIG. 18(A).

In an absorbent article 220 shown in FIG. 18, an entire periphery of a first leak preventer 10b rises upward. In this way, urine hardly leaks from the periphery of the first leak preventer 10b.

Figure 19A:
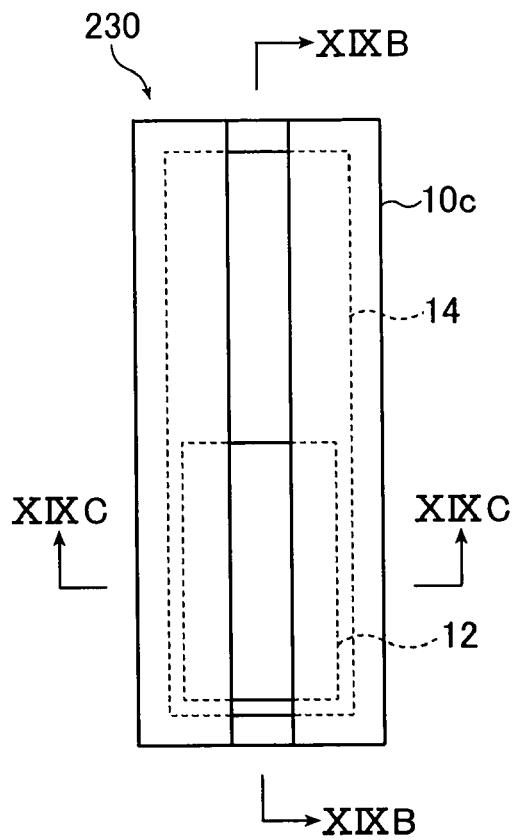
FIG. 19 show schematic diagrams each showing another example of the absorbent article of the present invention.
Figure 19B:
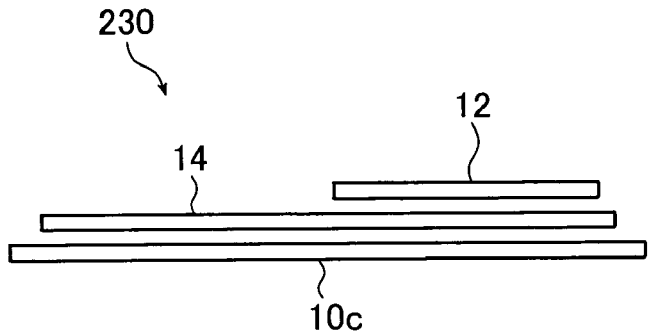
Figure 19C:
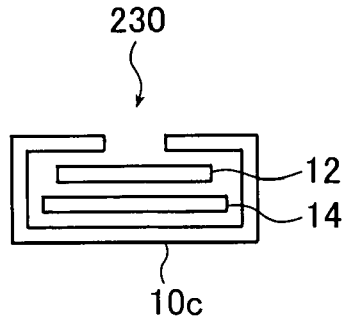

FIG. 19 are schematic diagrams each showing another example of the absorbent article of the present invention. FIG. 19(A) is a plan view. FIG. 19(B) is a longitudinal end view taken along the line XIXB-XIXB of FIG. 19(A), and FIG. 19(C) is a lateral end view taken along the line XIXC-XIXC of FIG. 19(A).

In an absorbent article 230 shown in FIG. 19, both right and left sides of a first leak preventer 10c rise upward to form side walls, and the side walls are folded inward. In this way, urine hardly leaks from the right and left sides of the first leak preventer 10c. Further, a space formed by the side walls serves as a passage, to thereby accelerate transfer of the urine to a rear part of the absorber 14.

Figure 20A:
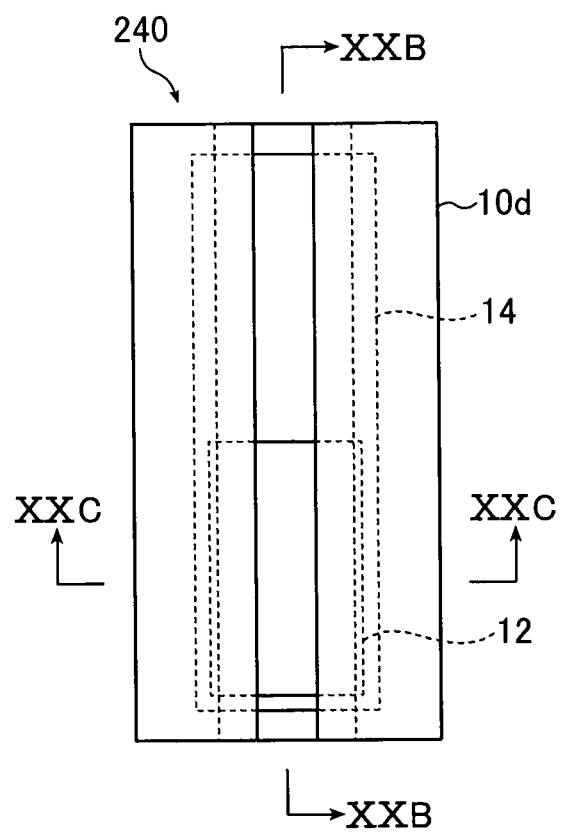
FIG. 20 show schematic diagrams each showing still another example of the absorbent article of the present invention.
Figure 20B:
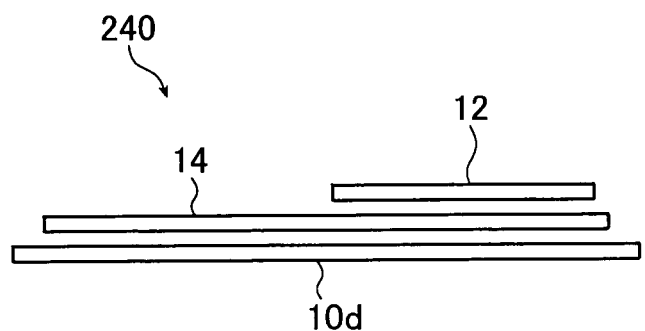
Figure 20C:
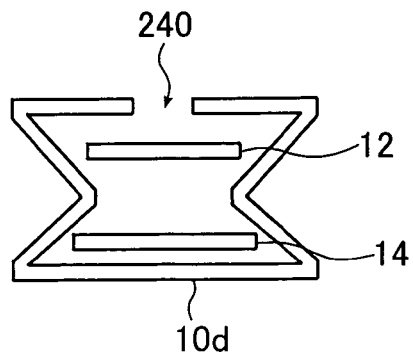

FIG. 20 are schematic diagrams each showing still another example of the absorbent article of the present invention. FIG. 20(A) is a plan view. FIG. 20(B) is a longitudinal end view taken along the line XXB-XXB of FIG. 20(A), and FIG. 20(C) is a lateral end view taken along the line XXC-XXC of FIG. 20(A).

An absorbent article 240 shown in FIG. 20 is basically the same as the absorbent article 230, but differs in that right and left side walls of a first leak preventer 10d are formed into folded-shape. In this way, a volume of a space formed by the first leak preventer 10d increases, to thereby increase an amount of the absorber 14 and increase a urine absorption amount.

Figure 21:
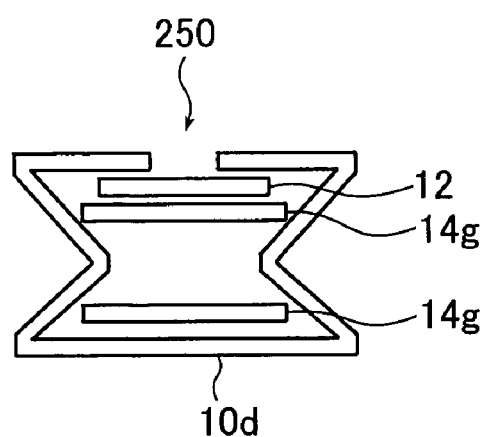
FIG. 21 shows schematic diagrams showing yet another example of the absorbent article of the present invention.

FIG. 21 is a schematic diagram showing a yet another example of the absorbent article of the present invention. FIG. 21 is a lateral end view.

An absorbent article 220 shown in FIG. 21 is basically the same as the absorbent article 210, but differs in that an absorber 14g as two layers is provided.

Figure 22A:
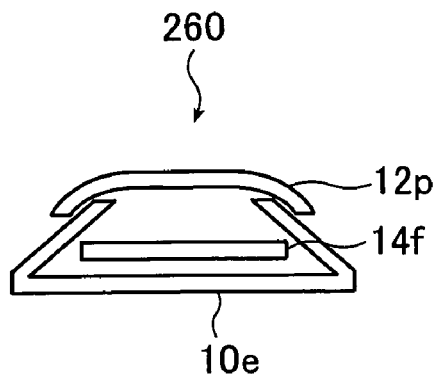
FIG. 22 show schematic diagrams each showing still yet another example of the absorbent article of the present invention.
Figure 22B:
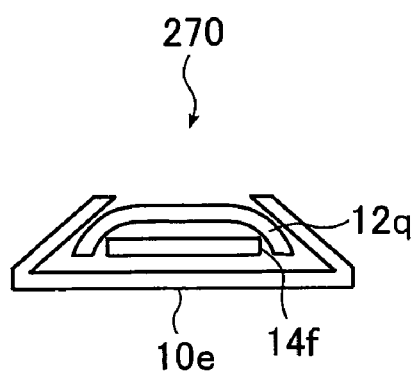

FIG. 22 are schematic diagrams each showing still yet another example of the absorbent article of the present invention. FIGS. 22(A) and 22(B) are each a lateral end view.

In an absorbent article 260 shown in FIG. 22(A), both right and left sides of a first leak preventer 10e rise upward and inward to form side walls. Both right and left ends of a second leak preventer 12p come down to cover the right and left side walls of the first leak preventer 10e.

An absorbent article 270 shown in FIG. 22(B) is basically the same as the absorbent article 260, but differs in that both right and left ends of a second leak preventer 12q come down to cover both right and left ends of the absorber 14f.

FIG. 23 are schematic diagrams showing various examples of a positional relationship between the first leak preventer, in which right and left side walls are formed into folded-shape, and the second leak preventer. FIGS. 23(A) to 23(O) are each a lateral end view. In FIG. 23, an unshaded member represents the first leak preventer, and a hatched member represents the second leak preventer. In FIG. 23, the absorber is omitted.

FIG. 24 are schematic diagrams showing various other examples of a positional relationship between the first leak preventer, in which right and left side walls are formed into folded-shape, and the second leak preventer. FIGS. 24(A) to 24(H) are each a lateral end view. In FIG. 24, an unshaded member represents the first leak preventer, and a hatched member represents the second leak preventer. A diagonally shaded member represents the absorber.

Of those, a preferable positional relationship includes an absorber provided in at least two of two or more stepped spaces defined by right and left side walls of the first leak preventer formed into folded-shape. Specific examples thereof include those shown in FIGS. 24(C) to 24(H). In this way, two or more layers of absorbers provide increased urine absorption capacity.

Figure 35A:
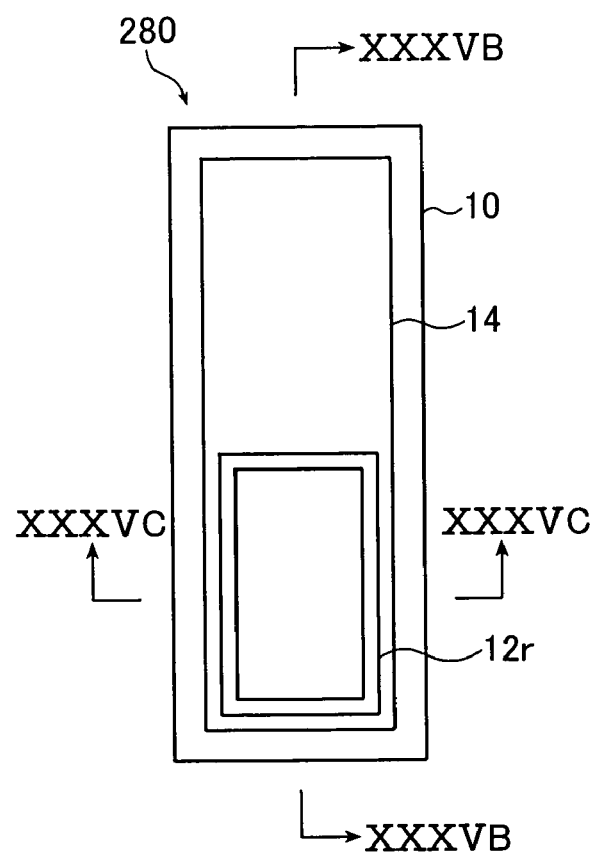
FIG. 35 show schematic diagrams each showing an example of the absorbent article of the present invention.
Figure 35B:
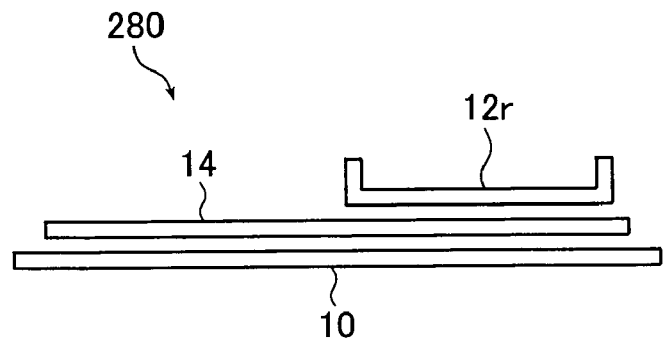
Figure 35C:
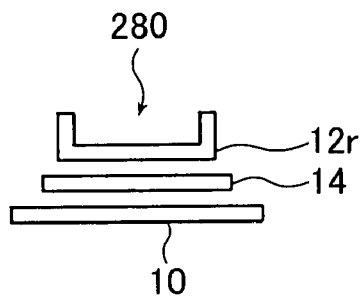

FIG. 35 are schematic diagrams each showing an example of the absorbent article of the present invention. FIG. 35(A) is a plan view. FIG. 35(B) is a longitudinal end view taken along the line XXXVB-XXXVB of FIG. 35(A), and FIG. 35(C) is a lateral end view taken along the line XXXVC-XXXVC of FIG. 35(A).

In an absorbent article 280 shown in FIG. 35, an entire periphery of a second leak preventer 12r rises upward. When a part or entire periphery of the second leak preventer rises upward as described above, feces hardly leaks from the periphery of the second leak preventer.

Hereinafter, the present invention will be described in more detail by way of specific embodiments.

Embodiment 1

Figure 25:
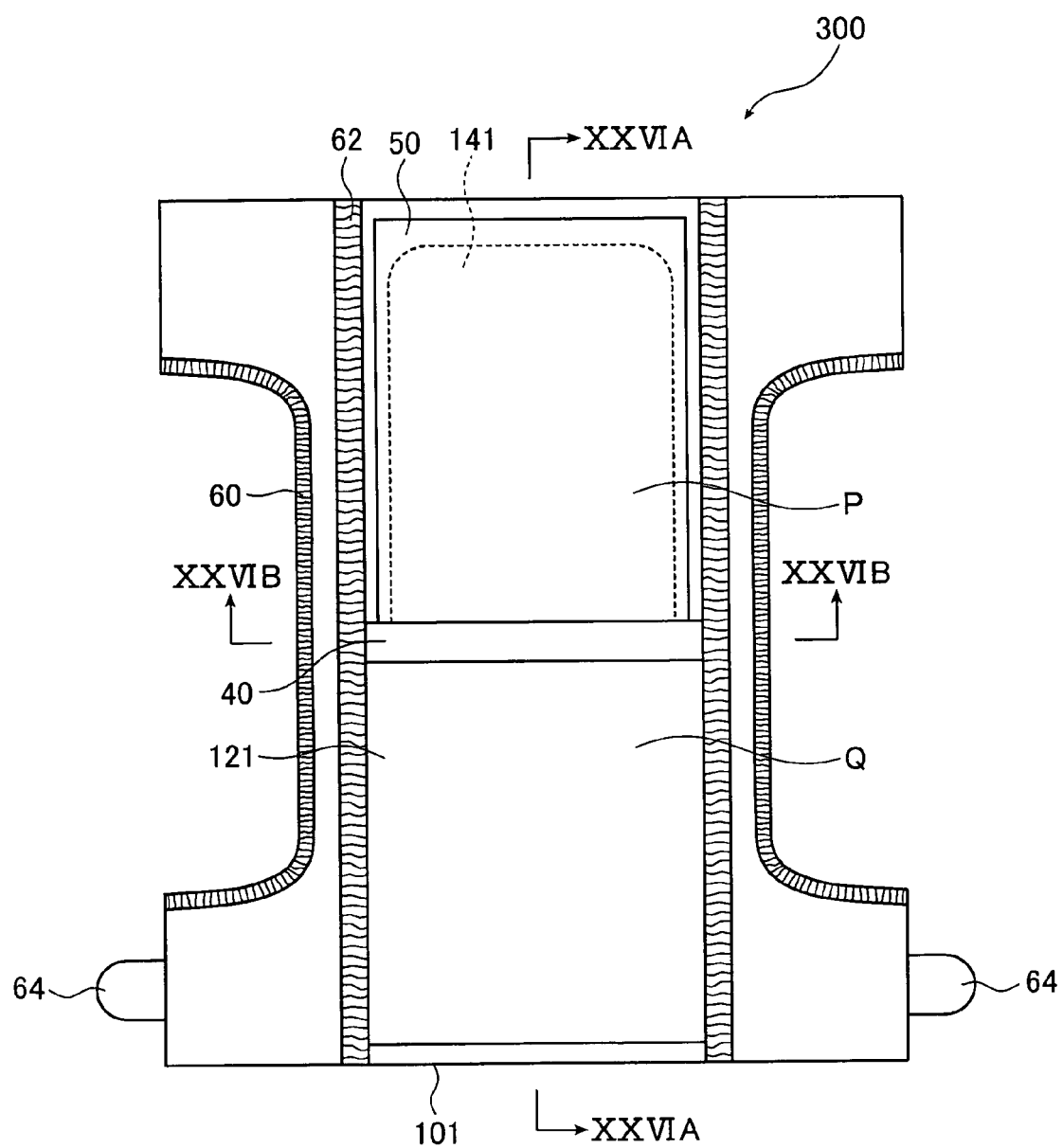
FIG. 25 is a schematic diagram showing an absorbent article of the present invention according to an embodiment of a tape-type diaper.
Figure 26A:
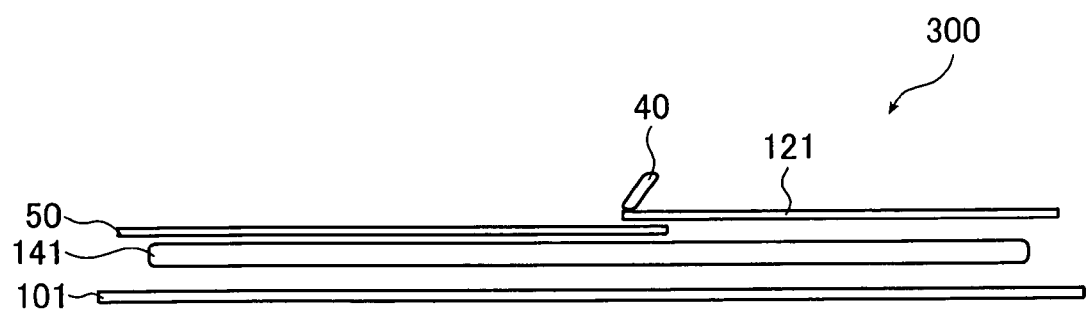
FIG. 26 show schematic diagrams each showing the absorbent article of the present invention according to the embodiment of a tape-type diaper.
Figure 26B:
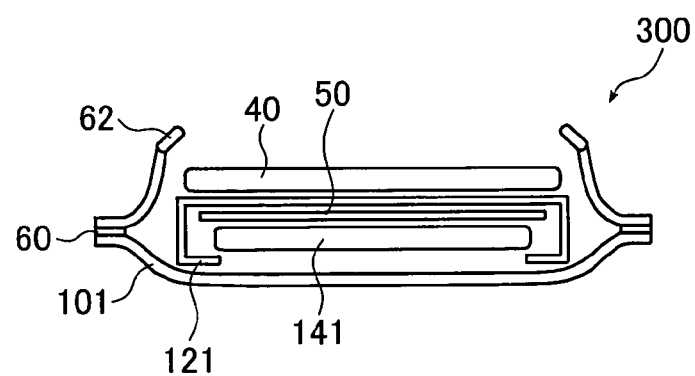

FIGS. 25 to 27 are schematic diagrams each showing an absorbent article of the present invention according to an embodiment of a tape-type diaper. FIG. 25 is a plan view. FIG. 26(A) is a longitudinal end view taken along the line XXVIA-XXVIA of FIG. 25, and FIG. 26(B) is a lateral end view taken along the line XXVIB-XXVIB of FIG. 25. FIG. 27 is a perspective view showing a state of the absorbent article worn.

In an absorbent article 300, a first leak preventer 101 in sheet form has a shape of a rectangle with a slightly narrow longitudinal center part, and the first leak preventer 101 has a bonding tape 64 on both rear ends.

A second leak preventer 121 in sheet form is provided in an upper rear part of the first sheet leak preventer 101. A substantially rectangular absorber 141 is provided above the first leak preventer 101 from a front part thereof beneath the second leak preventer 121. Both right and left sides of the second leak preventer 121 come down to form side walls. The side walls are folded inward to cover the absorber 141. In FIG. 26(A), the first leak preventer 101 and the second leak preventer 121 are completely separated from each other, but are actually bonded integrally at front and rear ends of the absorbent article 300, to thereby prevent leak of the urine or the feces.

In a vicinity of a longitudinal center part, a rod-like urine/feces stopping member 40 having a substantially elliptical section is provided. A front side from the rod-like urine/feces stopping member 40 serves as a urine receiving part P, and a rear side therefrom serves as a feces receiving part Q. The urine/feces stopping member 40 is inclined rearward slightly.

A skin contact sheet 50 is provided on the absorber 141. Being provided with the skin contact sheet 50 results in excellent surface touch of the absorbent article worn. The skin contact sheet is not particularly limited as long as it has body fluid permeability. A conventionally known top sheet can be used for the skin contact sheet. Specific examples thereof that may be used include: a nonwoven fabric of a synthetic fiber such as a PP nonwoven fabric, a PET nonwoven fabric, or a PE nonwoven fabric; and a dry nonwoven fabric obtained by mixing a hydrophilic fiber such as rayon or cotton, and a synthetic fiber.

The skin contact sheet 50 covers an upper surface of the absorber 141 from a position in front of a front end of the absorber 141 to a position behind a front end of the second leak preventer 121.

An outer gather 60, which is a stretchable strip member, is provided at a center part of each of right and left sides of the first leak preventer 101. Further, above the first leak preventer 101, an inner gather 62, which is a strip member, is provided on both right and left sides of the second leak preventer 121.

As shown in FIG. 27, when the absorbent article 300 is worn, front and rear ends of the first leak preventer 101 are bonded through the bonding tape 64, to thereby form one waist hole W and two leg holes LH.

Embodiment 2

Figure 28:
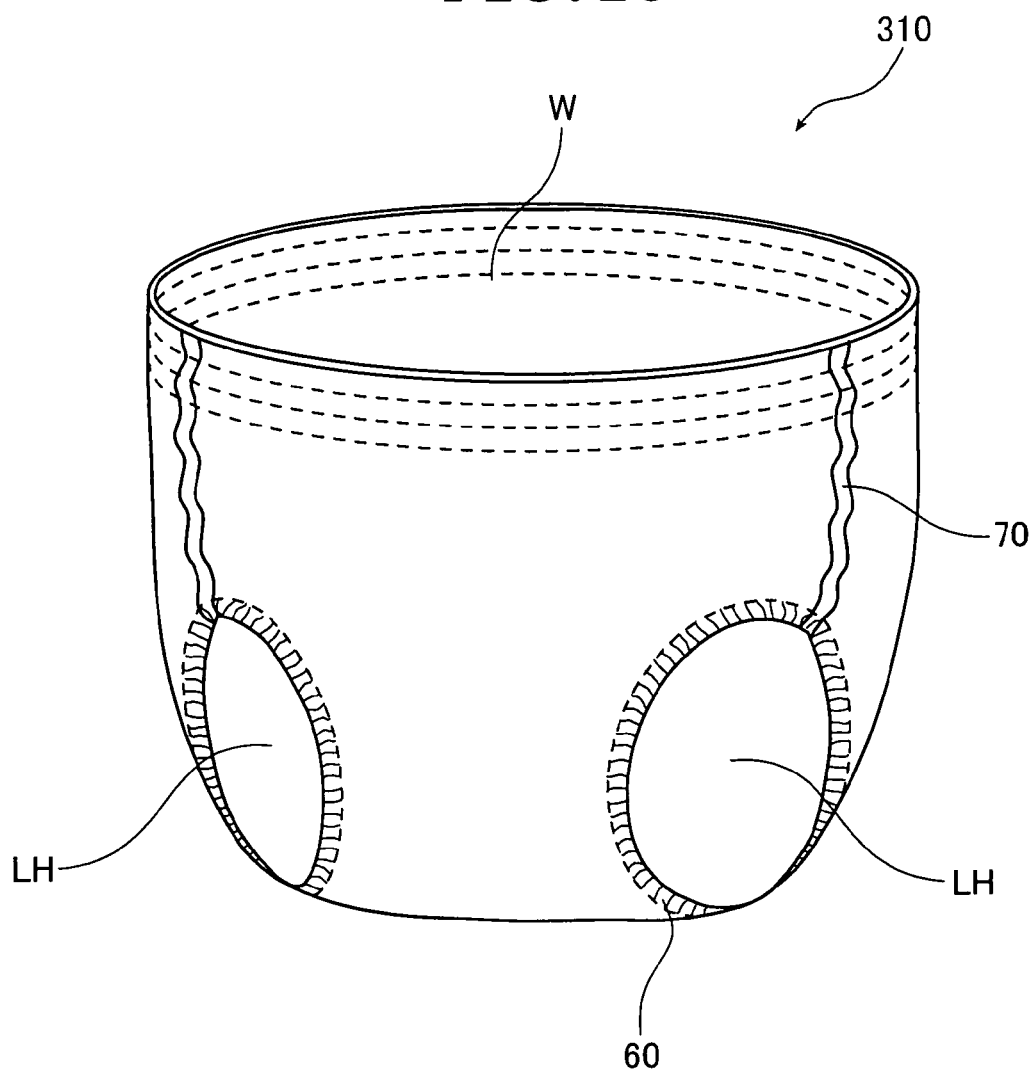
FIG. 28 is a schematic diagram showing an absorbent article of the present invention according to an embodiment of a tapeless-type diaper.
Figure 29:
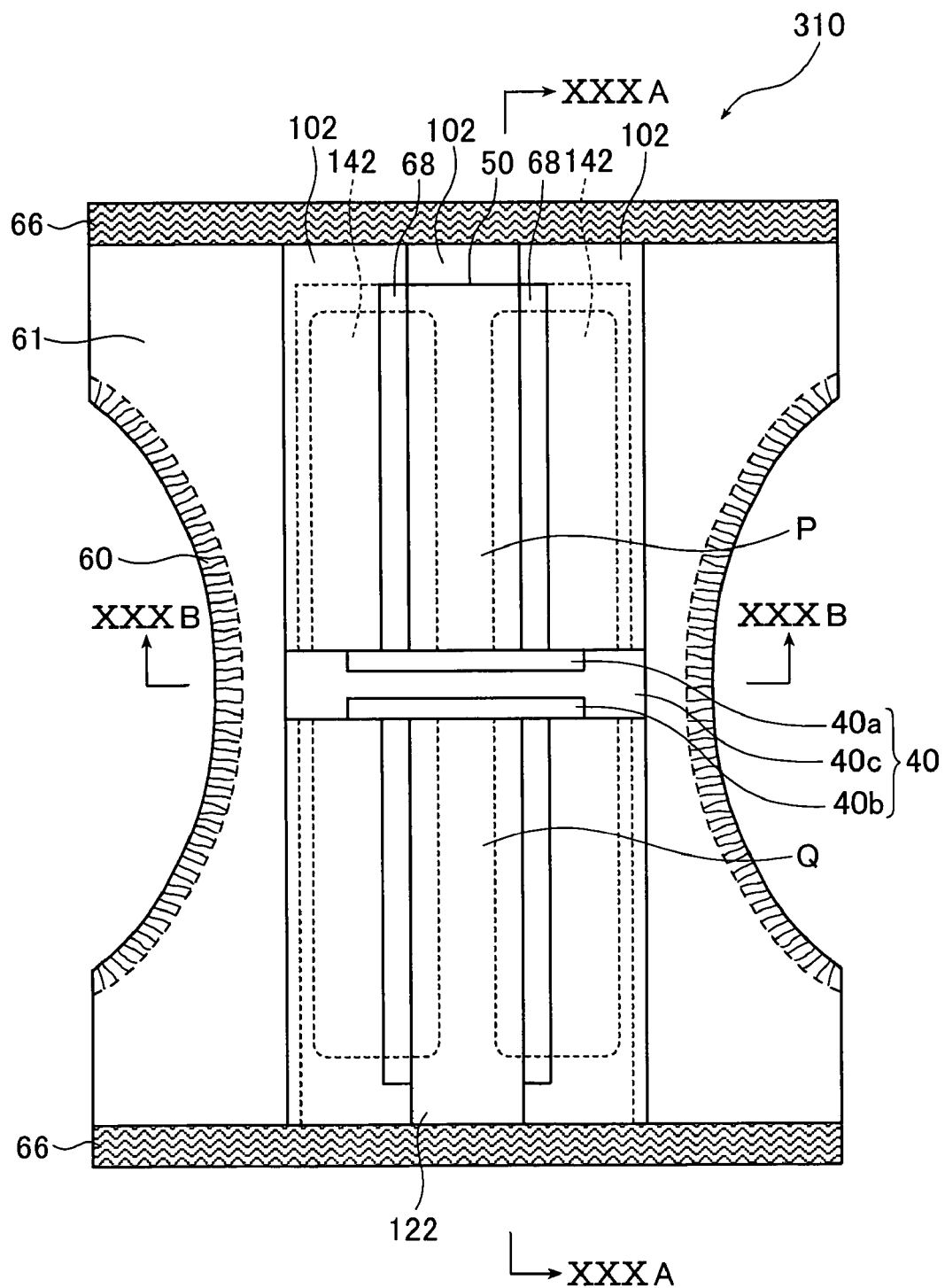
FIG. 29 is a schematic diagram showing the absorbent article of the present invention according to the embodiment of a tapeless-type diaper.
Figure 30A:
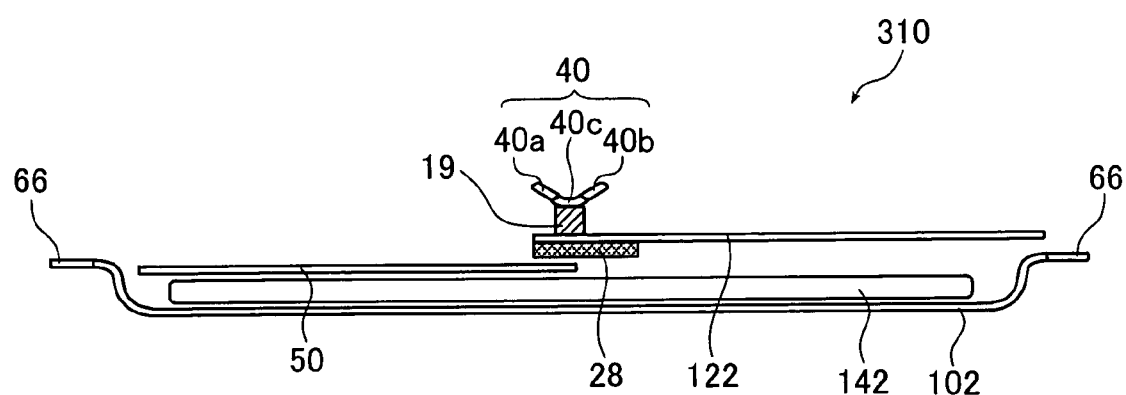
FIG. 30 show schematic diagrams each showing the absorbent article of the present invention according to the embodiment of a tapeless-type diaper.
Figure 30B:
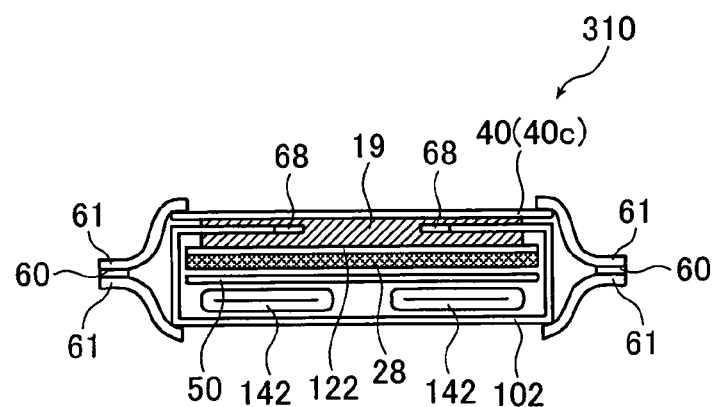

FIGS. 28 to 30 are schematic diagrams each showing an absorbent article of the present invention according to an embodiment of a tapeless-type diaper. FIG. 28 is a perspective view showing a state of the absorbent article worn. FIG. 30(A) is a longitudinal end view taken along the line XXXA-XXXA of FIG. 29, and FIG. 30(B) is a lateral end view taken along the line XXXB-XXXB of FIG. 29.

An absorbent article 310 shown in FIG. 28 has a front part and a rear part bonded through a bonding part 70, and has a shape of underpants having one waist hole W and two leg holes LH. FIG. 29 is a plan view of the absorbent article opened by separating the bonding part 70 of FIG. 28.

Both right and left sides of a first leak preventer 102 in sheet form rise upward to form side walls, which are folded inward. A peripheral shape retaining member 68 is provided across substantially the entire length of each of ends of the side walls of the first leak preventer 102.

The peripheral shape retaining member 68 has a function of retaining a shape of ends of the side walls, to thereby prevent efficiently leak of urine out of a body fluid receiving region. Further, when the absorbent article is worn, the peripheral shape retaining member 68 can prevent unevenness to a great extent at ends of the side walls.

A material for the peripheral shape retaining member 68 preferably has cushioning property (elasticity) and a certain thickness. Preferable examples thereof include: a foamed product (made of PU, PP, or PP/EVA, for example); a synthetic rubber sheet; a stretchable elastic film; a rubber filament; and a polyurethane filament.

When the absorbent article of the present invention is worn, a front part of the peripheral shape retaining member 68 is positioned on each of both sides of a urethral opening and an upper surface thereof is brought into contact with a body of a wearer, to thereby elastically fix the absorbent article and inhibit direct contact between the urethral opening and the absorbent article. Alternatively, even if the urethral opening and an absorbent article are brought into contact with each other, the peripheral shape retaining member 68 inhibits application of a large pressure on the urethral opening. In this way, a feeling of pressure on the urethral opening can be eliminated when the absorbent article is worn. A space formed between the two peripheral shape retaining members 68 serves as a passage for the urine. Thus, only the urethral opening of the wearer and a vicinity thereof get wet, and the wearer can urinate without wetting other sites.

On a front side of the absorbent article 310, genital organs are held between the two peripheral shape retaining members 68, to thereby prevent leak of urine to the outside. On a rear side of the absorbent article 310, the two peripheral shape retaining members 68 adhere to a skin of a wearer along round buttocks, to thereby prevent leak of feces, in particular, soft feces excreted, to the outside. As a result, an inner gather and an outer gather are not necessary, although they may be provided. In this embodiment, an outer gather 60 alone is provided.

A second leak preventer 122 in sheet form is provided above the first leak preventer 102 in its rear part. An absorber 142 is formed into two tubes and provided separately on right and left sides above the first leak preventer 102 in its front part beneath the second leak preventer 122. The absorber 142 is held in a space formed by side walls of the first leak preventer 102 and is only partly exposed.

A process for forming an absorber into a tube may employ a process proposed by the inventors of the present invention in JP 10-314217 A. As described above, the absorber 142 is preferably formed into a tube for efficient absorption of the urine in a small space. To be specific, the absorber 142 formed into a tube allows passage of the urine through the tube and hardly causes blocking of the urine. Thus, the absorber 142 may have a longitudinally long continuous shape. Further, when the absorber 142 formed into a tube absorbs the urine, the absorber 142 is hardly deformed and a space is formed between the two swollen absorbers 142, to thereby assure passage of the urine.

The urine/feces stopping member 40 is provided in a vicinity of a longitudinal center part. A front side of the urine/feces stopping member 40 serves as a urine receiving part P, and a rear side thereof serves as a feces receiving part Q. The urine/feces stopping member 40 includes: a rod-like urine stopping part 40a and a rod-like feces stopping part 40b each having a substantially elliptical section; and a base part 40c in sheet form for bonding these stopping parts. The urine stopping part 40a inclines to a front side to prevent transfer of the urine to a rear side. The feces stopping part 40b inclines rearward to prevent transfer of the feces to a front side. The urine/feces stopping member 40 is provided across an entire lateral width of the first leak preventer 102.

A lower surface of the urine/feces stopping member 40 and an upper surface of a front end of the second leak preventer 122 are bonded directly at a center part through a bonding part 19, and are bonded on both right and left sides through folded parts of the side walls of the first leak preventer 102 and the peripheral shape retaining member 68. That is, the urine/feces stopping member 40, the second leak preventer 122, the folded parts of the side walls of the first leak preventer 102 and the peripheral shape retaining member 68 are bonded integrally through the bonding part 19. The bonding part 19 may be formed of an adhesive such as a heat sensitive adhesive.

A urine introduction part forming member 28 having liquid permeability is provided under a front end of the second leak preventer 122. Thus, the urine stopped by the urine stopping part 40a passes through the urine introduction part forming member 28 having liquid permeability and transfers beneath the second leak preventer 122.

Similarly to Embodiment 1, the skin contact sheet 50 is provided on the absorber 142. The skin contact sheet 50 covers an upper surface of the absorber 142 from a position in front of a front end of the absorber 142 to a position behind a front end of the second leak preventer 122.

An outer member 61 formed of a nonwoven fabric bonded to side edges of the first leak preventer 102, the skin contact sheet 50, the second leak preventer 122, and the urine/feces stopping member 40 is provided outside the side walls of the first leak preventer 102. An outer gather 60, which is a stretchable strip member, is provided at a center part of each of right and left sides of the outer member 61.

A waist gather 66 is provided at both front and rear ends of the first leak preventer 102 and outer member 61.

In Embodiment 2, the first leak preventer 102 and the second leak preventer 122 are each formed into a bag independent from each other, to thereby allow substantially complete separation of the urine and the feces.

Embodiment 3

Figure 31:
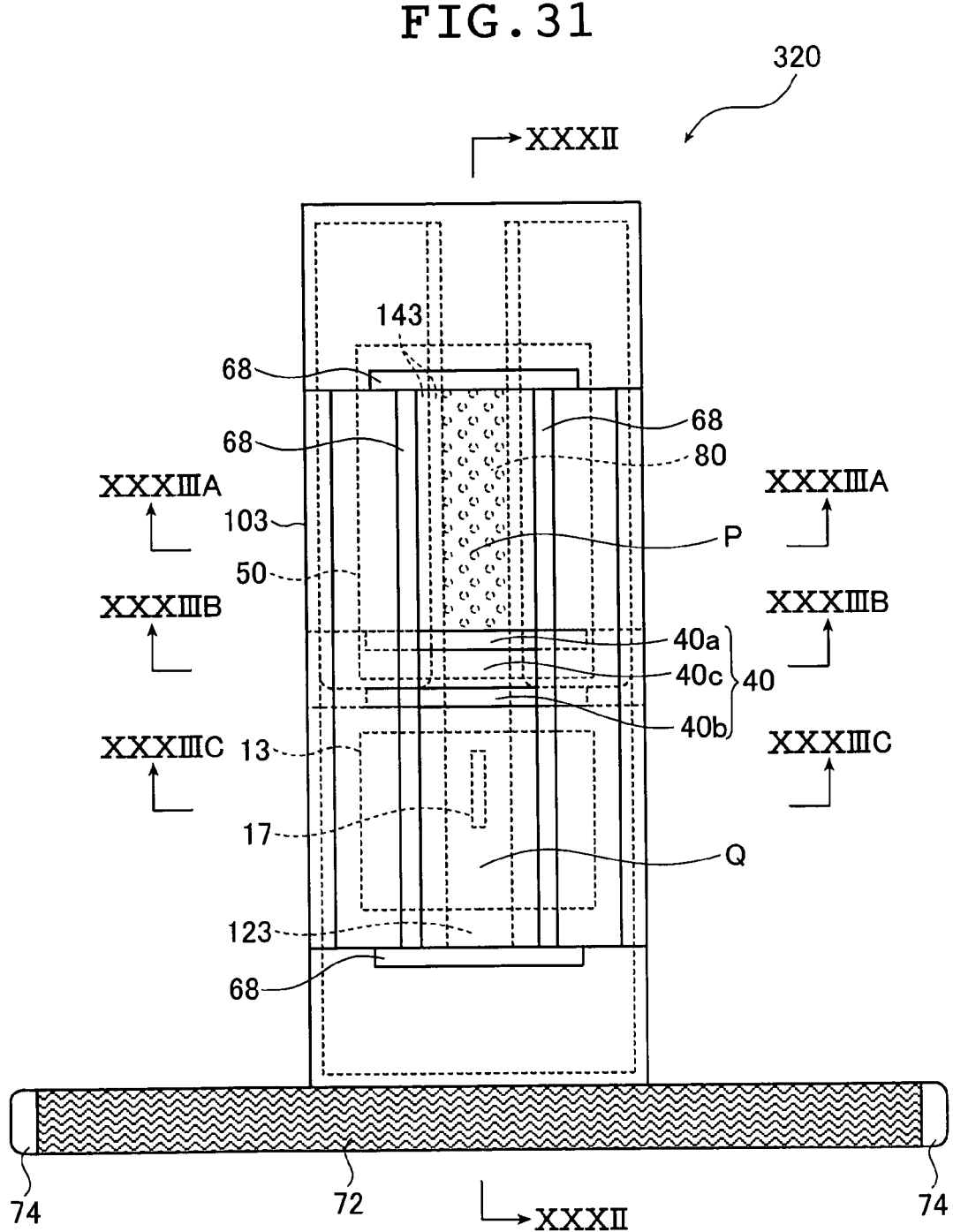
FIG. 31 is a schematic diagram showing an absorbent article of the present invention according to another embodiment of a tape-type diaper.
Figure 32:
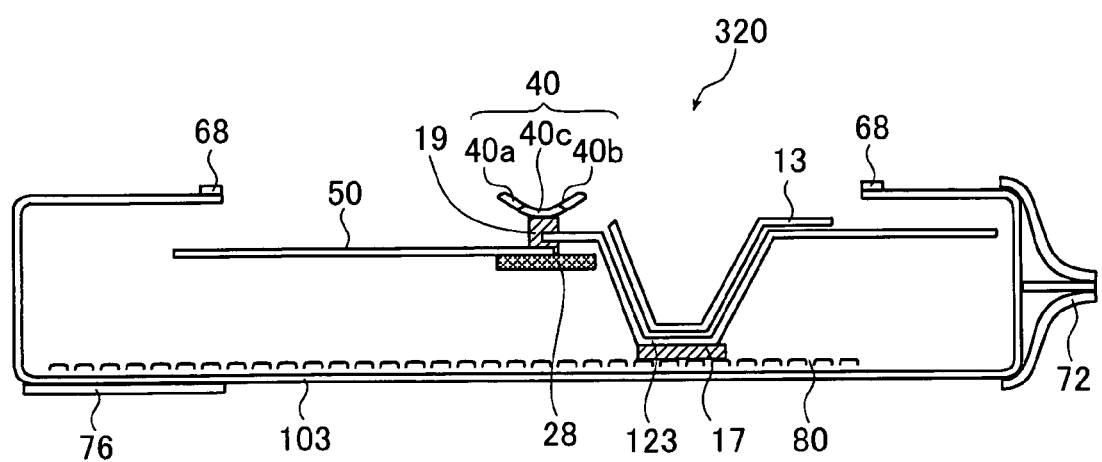
FIG. 32 is a schematic diagram showing the absorbent article of the present invention according to the embodiment of a tape-type diaper.
Figure 33A:
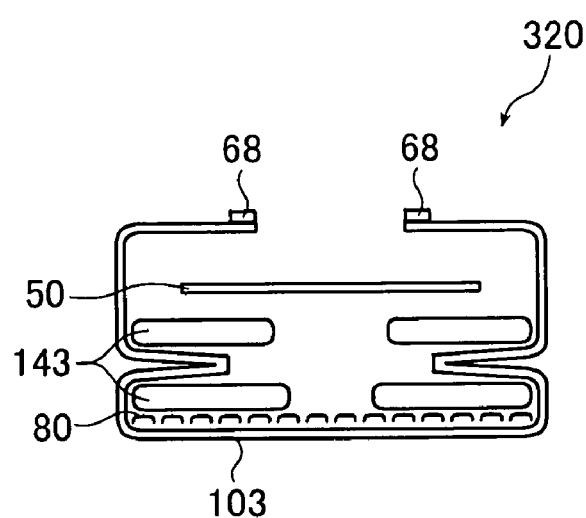
FIG. 33 show schematic diagrams each showing the absorbent article of the present invention according to the embodiment of a tape-type diaper.
Figure 33B:
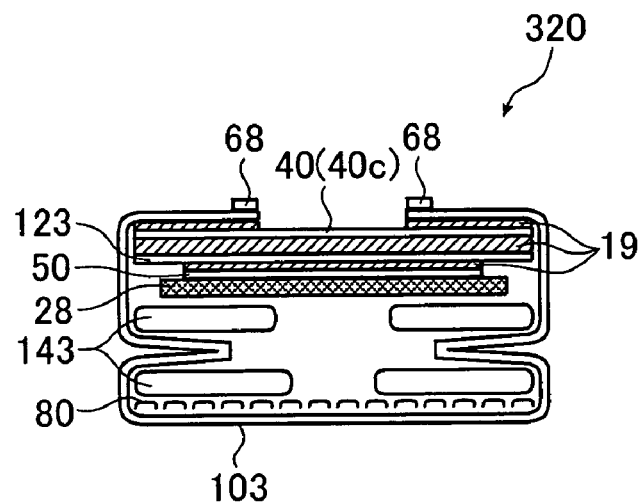
Figure 33C:
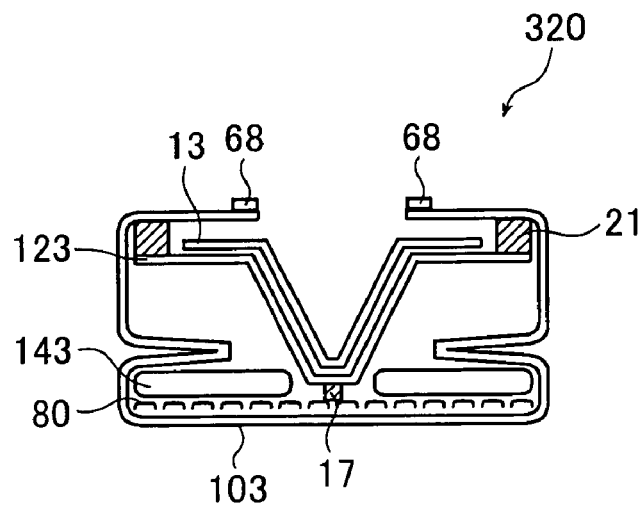
Figure 34:
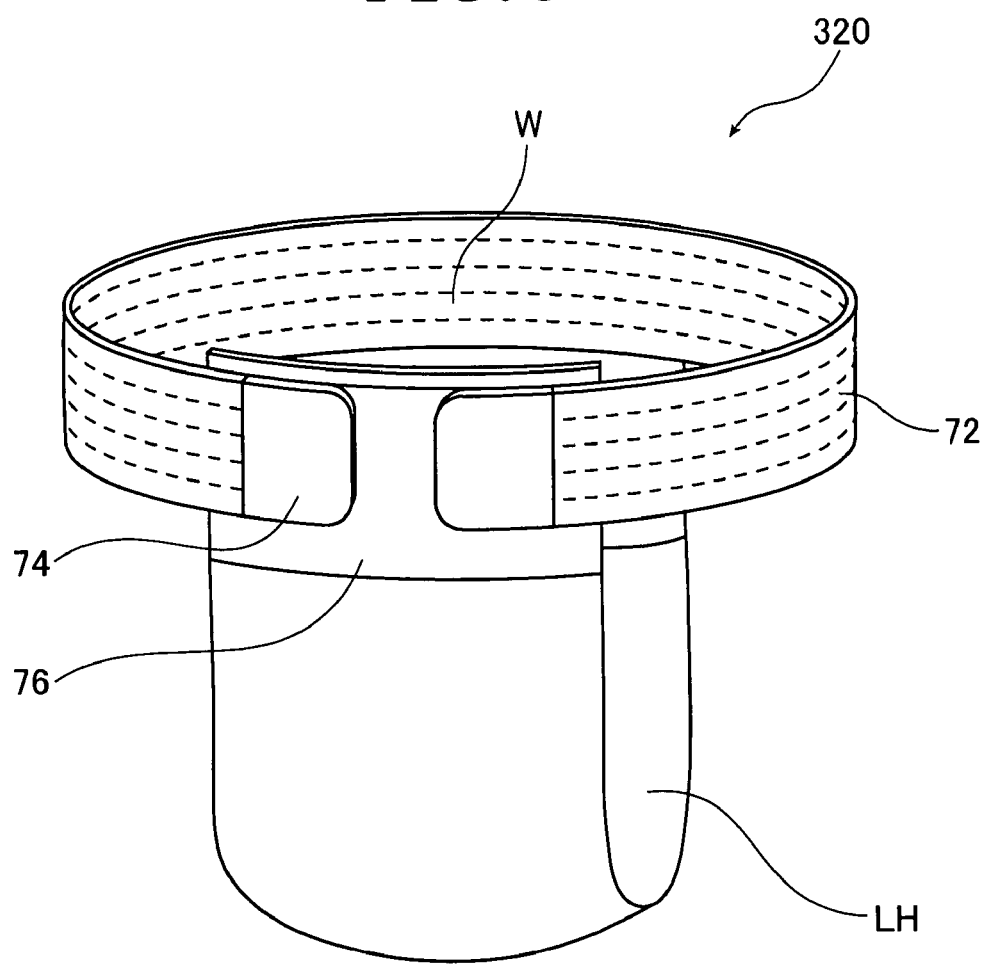
FIG. 34 is a schematic diagram showing the absorbent article of the present invention according to the embodiment of a tape-type diaper.

FIGS. 31 to 34 are each a schematic diagram showing an absorbent article of the present invention according to another embodiment mode of a tape-type diaper. FIG. 31 is a plan view. FIG. 32 is a longitudinal end view taken along the line XXXII-XXXII of FIG. 31, and FIGS. 33(A) to 33(C) are lateral end views taken along the line XXXIIIA-XXXIIIA, the line XXXIIIB-XXXIIIB, and the line XXXIIIC-XXXIIIC of FIG. 31, respectively. FIG. 34 is a perspective view of a state of the absorbent article worn.

In an absorbent article 320, front, rear, right, and left sides of a first leak preventer 103 in sheet form rise upward to form walls, which are folded inward. A peripheral shape retaining member 68 is provided to form a rectangle on each end of the walls of the first leak preventer 103.

When the absorbent article of the present invention is worn, front parts of the peripheral shape retaining members 68 are positioned on right, left, and front sides of a urethral opening and upper surfaces thereof are brought into contact with a body of a wearer, to thereby elastically fix the absorbent article and inhibit direct contact between the urethral opening and the absorbent article. Alternatively, even if the urethral opening and an absorbent article are brought into contact with each other, the peripheral shape retaining member 68 inhibits application of a large pressure on the urethral opening. In this way, a feeling of pressure on the urethral opening can be eliminated when the absorbent article is worn. A space formed between the two right and left peripheral shape retaining members 68 serves as a passage for the urine. Thus, only the urethral opening of the wearer and a vicinity thereof get wet, and the wearer can urinate without wetting other sites.

On a front side of the absorbent article 320, genital organs are held between the two right and left peripheral shape retaining members 68. The peripheral shape retaining members 68 at a front side adheres to a body of the wearer, and a front wall of the first leak preventer 103 is formed into a bag, to thereby prevent very efficiently leak of the urine to the outside. In particular, the effect is generally significant in a prone position in which the urine is liable to leak from the front side.

On a rear side of the absorbent article 320, the peripheral shape retaining members 68 adhere to a skin of the wearer along round buttocks. Further, the peripheral shape retaining members 68 at rear side adheres to the body of the wearer, and a rear wall of the first leak preventer 103 is formed into a bag, to thereby prevent very efficiently leak of the feces to the outside. In particular, the effect is generally significant in a supine position in which the feces, in particular, soft feces are liable to leak from the rear side. As a result, an inner gather and an outer gather are not necessary. This embodiment causes no tightening of the body of the wearer and provides excellent wearability. However, the inner gather and the outer gather may be provided.

Right and left side walls of the first leak preventer 103 are formed into folded-shape, and are divided into two stepped spaces of upper and lower spaces by folded parts. In this way, a larger amount of urine can be absorbed, and the absorbent article can be worn for a long period of time.

A second leak preventer 123 in sheet form is provided in a rear part of an upper space defined by the first leak preventer 103. A substantially rectangular absorbers 143 are provided separately on right and left sides from a front part of a lower space defined by the first leak preventer 103 beneath the second leak preventer 123, and is provided in a front part of the upper space of the first leak preventer 103. That is, the absorber 143 is formed in two layers on a front side of the absorbent article 320, and formed in one layer on a rear side thereof. The absorber 143 is held in a space formed by the side walls of the first leak preventer 103, and is only partly exposed.

In this way, only one layer of the absorber 143 is present under the second leak preventer 123, and thus is liable to sag down when the absorber 143 receives feces. That is, an amount of the feces to be received increases. In particular, in this embodiment, a front center part of the second leak preventer 123 is bonded to a member thereunder (liquid guide sheet 80 in this case) through the bonding part 17, and thus a volume of a feces receiving region increases in advances.

The absorber 143 is separated on right and left sides, and thus a volume of a center part increases further when the absorber 143 absorbs urine.

The urine/feces stopping member 40 is provided in a vicinity of a longitudinal center part. A front side from the urine/feces stopping member 40 serves as a urine receiving part P, and a rear side therefrom serves as a feces receiving part Q. The urine/feces stopping member 40 includes: a rod-like urine stopping part 40a and a rod-like feces stopping part 40b each having a substantially elliptical section; and a base part 40c in sheet form for bonding the stopping parts. The urine stopping part 40a inclines frontward to prevent transfer of the urine to a rear side. The feces stopping part 40b inclines rearward to prevent transfer of the feces to a front side. The urine/feces stopping member 40 is provided across the entire lateral width of the first leak preventer 103.

A lower surface of the urine/feces stopping member 40 and an upper surface of a front end of the second leak preventer 123 are bonded directly through the bonding part 17. The bonding part 17 may be formed of an adhesive such as a heat sensitive adhesive.

The urine introduction part forming member 28 having liquid permeability is provided under a front end of the second leak preventer 123. Thus, the urine stopped by the urine stopping part 40a passes through the urine introduction part forming member 28 having liquid permeability and transfers beneath the second leak preventer 123.

Upper surfaces of both right and left sides of the second leak preventer 123 are bonded to side surfaces of the first leak preventer 103 through a bonding part 21, to thereby prevent leak of the feces from the right and left sides of the second leak preventer 123.

A feces disposing sheet 13 is provided above the second leak preventer 123. The feces disposing sheet serves to absorb water content of feces, in particular, soft feces to inhibit wide spreading of the feces. A feces disposing sheet also serves as a skin contact sheet when feces are not excreted.

For example, an absorbent nonwoven fabric formed of pulp or the like is preferably used as the feces disposing sheet. To be specific, Kinocloth available from Oji Kinocloth Co., Ltd. is preferably used.

Similarly to Embodiment 1, the skin contact sheet 50 is provided on the absorber 143 in an upper space defined by the first leak preventer 103. The skin contact sheet 50 covers the upper surface of the absorber 143 from a position in front of a front end of the absorber 143 to a position behind a front end of the second leak preventer 123.

The liquid guide sheet 80 is provided under the absorber 143 in a lower space defined by the first leak preventer 103.

The liquid guide sheet 80 is not particularly limited as long as it has a structure including a passage allowing transfer of the urine, but preferably has no body fluid absorbing property or body fluid retaining property for rapid transfer of the urine. To be specific, an uneven sheet member (porous uneven sheet member) having pores on projected portion is preferably used.

A strip waist band 72 is provided at a rear end of the first leak preventer 103, and a removable member 74 is provided on each of both ends of the strip waist band 72. A removable member 76 is provided on a lower surface of a front end of the first leak preventer 103. The removable member 74 and the removable member 76 may be attached to or detached from each other freely, and are preferably formed of various hook and loop fasteners.

In Embodiment 3, the first leak preventer 103 and the second leak preventer 123 are each formed into a bag independent from each other, to thereby allow substantially complete separation of the urine and the feces.

In Embodiment 3, in a case where a wearer has difficulties in wearing the absorbent article by him- or her-self, a care giver can put on the absorbent article while checking a position of a urethral opening or anus of the wearer.

In the absorbent article of the present invention, the second leak preventer may be removable. In this case, after the second leak preventer receives feces, the second leak preventer may be removed and disposed. Then, an unused second leak preventer may be attached for repeated use of the absorbent article. Alternatively, the unused second leak preventer may not be attached, and the absorbent article may be used as a normal diaper in which the urine and the feces are not separated.

Further, when the absorbent article of the present invention includes the feces disposing sheet, the feces disposing sheet may also be removable. Then, an unused feces disposing sheet may be attached for repeated use of the absorbent article. Alternatively, the absorbent article may be used without attaching the unused feces processing sheet.

A structure of the removable second leak preventer or the like is not particularly limited. Examples thereof include: a structure in which the feces disposing sheet alone is removable; a structure in which the second leak preventer alone (without the feces disposing sheet) is removable; a structure in which the second leak preventer and the urine/feces stopping member are removable; and a structure in which the second leak preventer, the urine/feces stopping member, and the urine introduction part forming member are removable. In a case where the urine/feces stopping member is removable, a part (urine stopping part or feces stopping part, for example) of the urine/feces stopping member may removable or the entire urine/feces stopping member may be removable.

The removable members may be removable independently, or removable together.

As described above, the absorbent article of the present invention has been described in detail based on embodiment modes shown in the drawings. However, the present invention is not limited thereto, and structures of the respective members may be replaced by arbitrary structures which may exhibit similar functions.

The structures of the respective members of embodiment modes may be combined arbitrarily as other embodiment modes.

The absorbent article of the present invention may suitably be used as an absorbent article for an adult male, an adult female, or a child.

EXAMPLES

Hereinafter, the present invention will be described in more detail by referring to examples. However, the present invention is not limited thereto.

As described below, a test on wearability was performed by using the absorbent article of the present invention and a commercially available absorbent article.

1. Absorbent Article

In Example, the absorbent article of the present invention shown in FIGS. 31 to 34 was used. A super absorbent sheet prepared by coating SAP-dispersed slurry on a nonwoven fabric (MegaThin (trade name), available from Japan Absorbent Technology Institute, SAP amount: 140 g/m$^2$) was used as an absorber.

Table 1 shows a content of the super absorbent sheet, designed dehydrated water-absorption amount, and designed free water-absorption amount for each part of the absorbent article. The designed free water-absorption amount was determined in accordance with JIS K7223-1996 "Testing method for water-absorption capacity of super absorbent polymers". The designed dehydrated water-absorption amount was determined by centrifuging the absorbent article at 1,000 G for 10 min for dehydration, after measurement of the designed free water-absorption amount.

TABLE 1

|  | Content of super absorbent sheet (g) | Designed free water-absorption amount (mL) | Designed dehydrated water-absorption amount (mL) |
| --- | --- | --- | --- |
| Front part | 8.0 | 400 | 240 |
| Rear part | 4.0 | 200 | 120 |
| Total | 12.0 | 600 | 360 |

2. Test on Wearability

The absorbent article was put on each of four healthy subjects (male 1: 38 years old; male 2: 64 years old; female 1: 32 years old; and female 2: 54 years old) as wearers each having a healthy urination mechanism and a healthy bowel mechanism, and the wearers each urinated and defecated as described below.

The wearers each maintained a standing position, a sitting position, a recumbent position, or a supine position, and urinated when the wearer had a desire to urinate. After the urination was completed, the absorbent article was removed to measure a urine absorption amount. The wearers each put on the same absorbent article and urinated, and the urine absorption amount was measured in the same manner.

Then, the wearers each put on the same absorbent article for testing in the standing position and the sitting position, and defecated when the wearer had a desire to defecate. After the defecation was completed, the absorbent article was removed to measure an amount of feces captured. Further, the presence or absence of soil on the absorbent article and the wearer, and a separation level of the urine and the feces were observed.

Table 2 shows average urine absorption amounts of the four wearers for the first urination and the second urination.

Table 2 clearly shows that the urine absorption amount greatly exceeded the designed dehydrated water-absorption amount for testing in any position. Of those, the urine absorption amount was at a high level comparable to that of the designed free water-absorption amount for testing in the standing position and the sitting position.

TABLE 2

|  | First urination (mL) | Second urination (mL) | Total (mL) |
| --- | --- | --- | --- |
| Standing position | 340 | 280 | 620 |
| Sitting position | 370 | 220 | 590 |
| Recumbent position | 270 | 230 | 500 |
| Supine position | 300 | 250 | 550 |

Table 3 shows the amount of feces captured and the presence or absence of soil on the absorbent article and wearer.

Table 3 clearly shows that no soil was observed on the absorbent article after defecation, or soil was slightly observed thereon.

No soil was observed on the wearer after defecation. Here, a buttocks region of the wearer refers to a region of buttocks excluding a vicinity of an anus. Thus, no observation of soil in the region of buttocks excluding the vicinity of the anus, which is soiled with defecation, indicates that the feces was captured assuredly in a feces receiving part.

Further, the urine and the feces were completely separated for all the wearers and were not mixed.

TABLE 3

|  | MALE 1 (g) | MALE 2 (g) | FEMALE 1 (g) | FEMALE 2 (g) |
| --- | --- | --- | --- | --- |
| Standing position | — | 100 | — | 75 |
| Sitting position | 85 | 50 | 45 | 32 |
| Soil on absorbent article other than feces receiving part | Slight soil on periphery of urine/feces stopping member | None | Slight soil on periphery of urine/feces stopping member | None |
| Soil in region of wearer's buttocks region | None | None | None | None |

The invention claimed is:

1. An absorbent article configured to be worn by a user, where the article has a front side corresponding to a front side of a body of the user when the article is worn by the user, and a rear side corresponding to a rear side of the body of the user when the article is worn by the user, the article comprising:
a first leak preventer in sheet form extending from the front side of the absorbent article to the rear side of the absorbent article, the first leak preventer having a front part disposed on the front side of the absorbent article and a rear part disposed on the rear side of the absorbent article;
a second leak preventer in sheet form for receiving feces excreted from an anus of the user disposed above an upper side of the first leak preventer, the second leak preventer being positioned over the rear part of the first leak preventer, wherein the second leak preventer does not substantially extend over the front part of the first leak preventer and does not include any perforation so as to prevent the feces from permeating or passing through the second leak preventer and the second leak preventer is closer to a skin of the user than the first leak preventer when the article is worn by the user; and
an absorber containing a super absorbent polymer, capable of absorbing a body fluid, the absorber being disposed above an upper side of the first leak preventer and extending from the front part of the first leak preventer beneath the second leak preventer in at least one layer, and
a urine introduction part forming member bonded to a part of a lower surface of a front end or in a vicinity of the front end of the second leak preventer, the urine introduction part being provided to form a flow passage to flow the body fluid received on a front side of the absorber toward a rear side of the absorber.

2. The absorbent article according to claim 1, further comprising a urine/feces stopping member in the front end or in the vicinity of the front end of the second leak preventer.

3. The absorbent article according to claim 2, wherein the urine/feces stopping member is combined with the urine introduction part forming member.

4. The absorbent article according to claim 1, further comprising a urine/feces stopping member spaced apart from the second leak preventer.

5. The absorbent article according to claim 1, wherein the urine introduction part forming member has liquid permeability.

6. The absorbent article according to claim 1, further comprising a skin contact sheet provided on the absorber.

7. The absorbent article according to claim 5, further comprising a skin contact sheet provided on the absorber.

8. The absorbent article according to claim 6,
wherein the skin contact sheet is bonded to the urine introduction part forming member.

9. The absorbent article according to claim 7,
wherein the skin contact sheet is bonded to the urine introduction part forming member.

10. The absorbent article according to claim 1,
wherein a hollow space is provided between the second leak preventer and the absorber in a front end of the second leak preventer, the front end of the second leak preventer being disposed on the front side of the absorbent article, the hollow space opening out toward the front side of the absorbent article and being configured as a part of the flow passage, and
the urine introduction part being provided between the lower surface of the front end of the second leak preventer and an upper surface of the absorber to maintain the hollow space.

11. The absorbent article according to claim 2,
wherein the urine introduction part forming member has liquid permeability.

12. The absorbent article according to claim 3,
wherein the urine introduction part forming member has liquid permeability.

13. The absorbent article according to claim 4,
wherein the urine introduction part forming member has liquid permeability.

14. The absorbent article according to claim 2,
further comprising a skin contact sheet provided on the absorber.

15. The absorbent article according to claim 3,
further comprising a skin contact sheet provided on the absorber.

16. The absorbent article according to claim 4,
further comprising a skin contact sheet provided on the absorber.

* * * * *